(12) United States Patent
Pulé et al.

(10) Patent No.: US 10,098,926 B2
(45) Date of Patent: *Oct. 16, 2018

(54) CELL

(71) Applicants: UCL BUSINESS PLC, London (GB); AUTOLUS LIMITED, London (GB)

(72) Inventors: Martin Pulé, London (GB); Shaun Cordoba, London (GB); Shimobi Onuoha, London (GB); Simon Thomas, London (GB)

(73) Assignees: UCL BUSINESS PLC, London (GB); AUTOLUS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/631,948

(22) Filed: Jun. 23, 2017

(65) Prior Publication Data

US 2017/0340704 A1 Nov. 30, 2017

Related U.S. Application Data

(63) Continuation of application No. 15/529,690, filed as application No. PCT/GB2015/054137 on Dec. 23, 2015.

(30) Foreign Application Priority Data

Dec. 24, 2014 (GB) .................................. 1423172.4

(51) Int. Cl.

| A61K 38/17 | (2006.01) |
|---|---|
| C07K 14/725 | (2006.01) |
| C12N 5/0783 | (2010.01) |
| A61K 35/17 | (2015.01) |
| C07K 14/705 | (2006.01) |
| C07K 16/28 | (2006.01) |
| A61K 39/00 | (2006.01) |

(52) U.S. Cl.
CPC .......... *A61K 38/1774* (2013.01); *A61K 35/17* (2013.01); *C07K 14/7051* (2013.01); *C07K 14/70521* (2013.01); *C07K 16/2803* (2013.01); *C12N 5/0636* (2013.01); *A61K 2039/505* (2013.01); *C07K 2317/622* (2013.01); *C07K 2319/03* (2013.01)

(58) Field of Classification Search
None
See application file for complete search history.

(56) References Cited

U.S. PATENT DOCUMENTS 7,052,906 B1 5/2006 Lawson et al.
2013/0266551 A1* 10/2013 Campana ........... C07K 16/2866
424/93.21

FOREIGN PATENT DOCUMENTS

| WO | WO-2013/123061 A1 | 8/2013 |
|---|---|---|
| WO | WO-2014/065961 A1 | 5/2014 |
| WO | WO-2014/124143 A1 | 8/2014 |
| WO | WO-2015/075468 A1 | 5/2015 |

OTHER PUBLICATIONS

Gerdes et al. (Front. Oncol. Dec. 18, 2014 doi: 10.3389/fonc.2014.00366, pp. 1-12) (Year: 2014).*
Kaiser (Science, 2006, 313: 1370) (Year: 2006).*
Krontiris and Capizzi (Internal Medicine, 4th Edition, Editor-in-chief Jay Stein, Elsevier Science, 1994 Chapters 71-72, pp. 699-729) (Year: 1994).*
Bejcek et al., Development and characterization of three recombinant single chain antibody fragments (scFvs) directed against the CD19 antigen, Cancer Res., 55(11):2346-51 (1995).
Campana et al., Human B cell development. I. Phenotypic differences of B lymphocytes in the bone marrow and peripheral lymphoid tissue, J. Immunol., 134(3):1524-30 (1985).
Campana et al., Immunophenotyping of leukemia, J. Immunol. Methods, 243(1-2):59-75 (2000).
Dijoseph et al., Antibody-targeted chemotherapy of B-cell lymphoma using calicheamicin conjugated to murine or humanized antibody against CD22, Cancer Immunol. Immunother., 54(1):11-24 (2005).
Dorken et al., HD39 (B3), a B lineage-restricted antigen whose cell surface expression is limited to resting and activated human B lymphocytes, J. Immunol., 136(12):4470-9 (1986).
Duong et al., Enhancing the specificity of T-cell cultures for adoptive immunotherapy of cancer, Immunotherapy, 3(1):33-48 (2011).
Engel et al., Identification of the ligand-binding domains of CD22, a member of the immunoglobulin superfamily that uniquely binds a sialic acid-dependent ligand, J. Exp. Med., 181(4):1581-6 (1995).
Grada et al., TanCAR: A Novel Bispecific Chimeric Antigen Receptor for Cancer Immunotherapy, Mol. Ther. Nucleic Acids, 2:e105 (2013).
Haso et al., Anti-CD22-chimeric antigen receptors targeting B-cell precursor acute lymphoblastic leukemia, Blood, 121(7):1165-74 (2013).
Hegde et al., Combinational targeting offsets antigen escape and enhances effector functions of adoptively transferred T cells in glioblastoma, Mol. Ther., 21(11):2087-101 (2013).
Herbst et al., B-cell depletion in vitro and in vivo with an afucosylated anti-CD19 antibody, J. Pharmacol. Exp. Ther., 335(1):213-22 (2010).
International Search Report and Written Opinion, International Application No. PCT/GB2015/054137, dated Jun. 6, 2016.
James et al., Antigen sensitivity of CD22-specific chimeric TCR is modulated by target epitope distance from the cell membrane, J. Immunol., 180(10):7028-38 (2008).
Jena et al., Driving CAR-based T-cell therapy to success, Curr. Hematol. Malig. Rep., 9(1):50-6 (2014).

(Continued)

*Primary Examiner* — Peter J Reddig
(74) *Attorney, Agent, or Firm* — Marshall, Gerstein & Borun LLP

(57) ABSTRACT

The present invention provides a cell which co-expresses a first chimeric antigen receptor (CAR) and second CAR at the cell surface, each CAR comprising an antigen-binding domain, wherein the antigen-binding domain of the first CAR binds to CD19 and the antigen-binding domain of the second CAR binds to CD22.

4 Claims, 17 Drawing Sheets

Specification includes a Sequence Listing.

(56) References Cited

OTHER PUBLICATIONS

John et al., The B cell coreceptor CD22 associates with AP50, a clathrin-coated pit adapter protein, via tyrosine-dependent interaction, J. Immunol., 170(7):3534-43 (2003).

Kansas et al., Transmembrane signals generated through MHC class II, CD19, CD20, CD39, and CD40 antigens induce LFA-1-dependent and independent adhesion in human B cells through a tyrosine kinase-dependent pathway, J. Immunol., 147(12):4094-12 (1991).

Krauss et al., Specificity grafting of human antibody frameworks selected from a phage display library: generation of a highly stable humanized anti-CD22 single-chain Fv fragment, Protein Eng., 16(10):753-9 (2003).

Kreitman et al., Phase I trial of anti-CD22 recombinant immunotoxin moxetumomab pasudotox (CAT-8015 or HA22) in patients with hairy cell leukemia, J. Clin. Oncol., 30(15):1822-8 (2012).

Lanitis et al., Chimeric antigen receptor T Cells with dissociated signaling domains exhibit focused antitumor activity with reduced potential for toxicity in vivo, Cancer Immunol. Res., 1(1):43-53 (2013).

Leonard et al., Phase I/II trial of epratuzumab (humanized anti-CD22 antibody) in indolent non-Hodgkin's lymphoma, J. Clin. Oncol., 21(16):3051-9 (2003).

Mason et al., Value of monoclonal anti-CD22 (p135) antibodies for the detection of normal and neoplastic B lymphoid cells, Blood, 69(3):836-40 (1987).

Meeker et al., A unique human B lymphocyte antigen defined by a monoclonal antibody, Hybridoma, 3(4):305-20 (1984).

Nicholson et al., Construction and characterisation of a functional CD19 specific single chain Fv fragment for immunotherapy of B lineage leukaemia and lymphoma, Mol. Immunol., 34(16-17):1157-65 (1997).

Pezzutto et al., Amplification of human B cell activation by a monoclonal antibody to the B cell-specific antigen CD22, Bp 130/140, J. Immunol., 138(1):98-103 (1987).

Pezzutto et al., CD19 monoclonal antibody HD37 inhibits anti-immunoglobulin-induced B cell activation and proliferation, J. Immunol., 138(9):2793-9 (1987).

Raponi et al., Flow cytometric study of potential target antigens (CD19, CD20, CD22, CD33) for antibody-based immunotherapy in acute lymphoblastic leukemia: analysis of 552 cases, Leuk. Lymphoma, 52(6):1098-107 (2011).

Riët,, Erhöhung der Antigen-Selektivität von T-Zellen durch Koexpression chimärer Antigen-Rezeptoren unterschiedlicher Spezifität, PhD thesis, Universität zu Köln (2010), English abstract.

Roguska et al., A comparison of two murine monoclonal antibodies humanized by CDR-grafting and variable domain resurfacing, Protein Eng., 9(10):895-904 (1996).

Schwarting et al., The monoclonal antibodies alpha S-HCL 1 (alpha Leu-14) and alpha S-HCL 3 (alpha Leu-M5) allow the diagnosis of hairy cell leukemia, Blood, 65(4):974-83 (1985).

Shih et al., Internalization and intracellular processing of an anti-B-cell lymphoma monoclonal antibody, LL2, Int. J. Cancer, 56(4):538-45 (1994).

Srivastava et al., Engineering CAR-T cells: Design concepts, Trends Immunol., 36(8):494-502 (2015).

Wen et al., The pan-B cell marker CD22 is expressed on gastrointestinal eosinophils and negatively regulates tissue eosinophilia, J. Immunol., 188(3):1075-82 (2012).

Wilkie et al., Dual targeting of ErbB2 and MUC1 in breast cancer using chimeric antigen receptors engineered to provide complementary signaling, J. Clin. Immunol., 32(5):1059-70 (2012).

Xiao et al., Identification and characterization of fully human anti-CD22 monoclonal antibodies, MAbs, 1(3):297-303 (2009).

Yazawa et al., Immunotherapy using unconjugated CD19 monoclonal antibodies in animal models for B lymphocyte malignancies and autoimmune disease, Proc. Natl. Acad. Sci. USA, 102(42):15178-83 (2005).

* cited by examiner

FIG. 4

FIGURE 5A
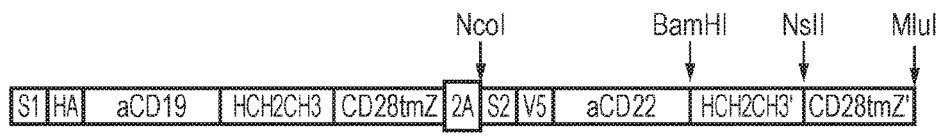
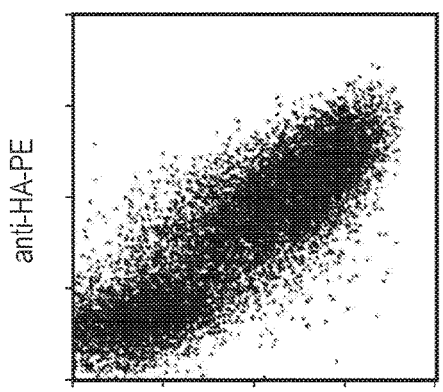
FIGURE 5B
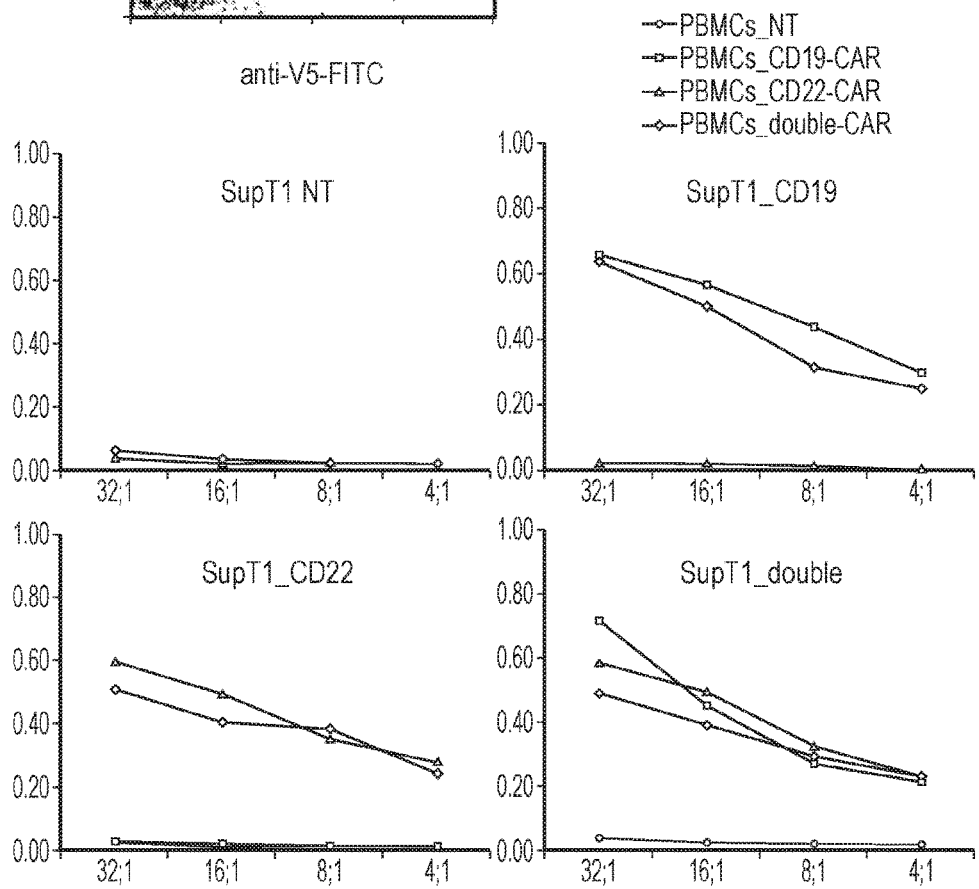
FIGURE 5C

| scFv | ka (1/Ms) | kd (1/s) | KD (nM) | n |
|---|---|---|---|---|
| CD19ALAb | $1.65 \pm 0.143 \times 10^5$ | $3.00 \pm 2.198 \times 10^{-4}$ | $1.1 \pm 0.2$ | 2 |
| FMC63 | $3.2 \pm 0.8 \times 10^5$ | $3.9 \pm 1.2 \times 10^{-4}$ | $1.3 \pm 0.7$ | 2 |

FIG. 8

CELL

INCORPORATION BY REFERENCE OF MATERIALS SUBMITTED ELECTRONICALLY

This application contains, as a separate part of the disclosure, a Sequence Listing in computer readable form (Filename: 52020A_Seqlisting.txt; Size: 59,714 bytes; Created: Jun. 16, 2017), which is incorporated by reference in its entirety.

FIELD OF THE INVENTION

The present invention relates to a cell which comprises more than one chimeric antigen receptor (CAR).

BACKGROUND TO THE INVENTION

A number of immunotherapeutic agents have been described for use in cancer treatment, including therapeutic monoclonal antibodies (mAbs), immunoconjugated mAbs, radioconjugated mAbs and bi-specific T-cell engagers.

Typically these immunotherapeutic agents target a single antigen: for instance, Rituximab targets CD20; Myelotarg targets CD33; and Alemtuzumab targets CD52.

The human CD19 antigen is a 95 kd transmembrane glycoprotein belonging to the immunoglobulin superfamily. CD19 is expressed very early in B-cell differentiation and is only lost at terminal B-cell differentiation into plasma cells. Consequently, CD19 is expressed on all B-cell malignancies apart from multiple myeloma. Since loss of the normal B-cell compartment is an acceptable toxicity, CD19 is an attractive CAR target and clinical studies targeting CD19 with CARs have seen promising results.

A particular problem in the field of oncology is provided by the Goldie-Coldman hypothesis: which describes that the sole targeting of a single antigen may result in tumour escape by modulation of said antigen due to the high mutation rate inherent in most cancers. This modulation of antigen expression may reduce the efficacy of known immunotherapeutics, including those which target CD19.

Thus a problem with immunotherapeutics targeted against CD19 is that a B-cell malignancy may mutate and become CD19-negative. This may result in relapse with CD19-negative cancers which are not responsive to CD19 targeted therapeutics. For example, in one paediatric study, Grupp et al. reported that half of all relapses following CD19-targeted chimeric antigen receptor therapy for B-acute Lymphoblastic leukaemia (B-ALL) were due to CD19-negative disease (56th American Society of Hematology Annual Meeting and Exposition).

There is thus a need for immunotherapeutic agents which are capable of targeting more than one cell surface structure to reflect the complex pattern of marker expression that is associated with many cancers, including CD19-positive cancers.

Chimeric Antigen Receptors (CARs)

Chimeric antigen receptors are proteins which graft the specificity of, for example, a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

It has been observed that using a CAR approach for cancer treatment, tumour heterogeneity and immunoediting can cause escape from CAR treatment. For example, in the study described by Grupp et al (2013; New Eng. J. Med 368:1509-1518, paper No 380, ASH 2014) CAR-modified T cell approach was used for the treatment of acute B-lymphocytic leukemia. In that clinical trial it was found that 10 patients with a complete remission after one month did relapse and 5 of them relapsed with CD19-negative disease.

There is thus a need for alternative CAR treatment approaches which address the problems of cancer escape and tumour heterogeneity.

Expression of Two CAR Binding Specificities

Bispecific CARs known as tandem CARs or TanCARs have been developed in an attempt to target multiple cancer specific markers simultaneously. In a TanCAR, the extracellular domain comprises two antigen binding specificities in tandem, joined by a linker. The two binding specificities (scFvs) are thus both linked to a single transmembrane portion: one scFv being juxtaposed to the membrane and the other being in a distal position.

Grada et al (2013, Mol Ther Nucleic Acids 2:e105) describes a TanCAR which includes a CD19-specific scFv, followed by a Gly-Ser linker and then a HER2-specific scFv. The HER2-scFv was in the juxta-membrane position, and the CD19-scFv in the distal position. The Tan CAR was shown to induce distinct T cell reactivity against each of the two tumour restricted antigens. This arrangement was chosen because the respective lengths of HER2 (632 aa/125 Å) and CD19 (280aa, 65 Å) lends itself to that particular spatial arrangement. It was also known that the HER2 scFv bound the distal-most 4 loops of HER2.

The problem with this approach is that the juxta-membrane scFv may be inaccessible due to the presence of the distal scFv, especially which it is bound to the antigen. In view of the need to choose the relative positions of the two scFvs in view of the spatial arrangement of the antigen on the target cell, it may not be possible to use this approach for all scFv binding pairs. Moreover, it is unlikely that the TanCar approach could be used for more than two scFvs, a TanCAR with three or more scFvs would be a very large molecule and the scFvs may well fold back on each other, obscuring the antigen-binding sites. It is also doubtful that antigen-binding by the most distal scFv, which is separated from the transmembrane domain by two or more further scFvs, would be capable of triggering T cell activation.

There is thus a need for an alternative approach to express two CAR binding specificities on the surface of a cell such as a T cell.

SUMMARY OF THE INVENTION

The present inventors have developed a CAR T cell which expresses two CARs at the cell surface, one specific for CD19 and one specific for CD22.

Thus in a first aspect the present invention provides a cell which co-expresses a first chimeric antigen receptor (CAR) and second CAR at the cell surface, each CAR comprising an antigen-binding domain, wherein the antigen-binding domain of the first CAR binds to CD19 and the antigen-binding domain of the second CAR binds to CD22.

The fact the one CAR binds CD19 and the other CAR binds CD22 is advantageous because some lymphomas and leukaemias become CD19 negative after CD19 targeting, (or possibly CD22 negative after CD22 targeting), so it gives a "back-up" antigen, should this occur.

The cell may be an immune effector cell, such as a T-cell or natural killer (NK) cell. Features mentioned herein in connection with a T cell apply equally to other immune effector cells, such as NK cells.

Each CAR may comprise:
(i) an antigen-binding domain;
(ii) a spacer; and
(iii) a trans-membrane domain.

Each CAR may comprise:
(i) an antigen-binding domain;
(ii) a spacer;
(iii) a trans-membrane domain;
(iv) an endodomain.

The spacer of the first CAR may be different to the spacer of the second CAR, such the first and second CAR do not form heterodimers.

The spacer of the first CAR may have a different length and/or configuration from the spacer of the second CAR, such that each CAR is tailored for recognition of its respective target antigen.

The antigen-binding domain of the second CAR may bind to a membrane-distal epitope on CD22. The antigen-binding domain of the second CAR may bind to an epitope on Ig domain 1, 2, 3 or 4 of CD22, for example on Ig domain 3 of CD22.

The antigen-binding domain of the first CAR may bind to an epitope on CD19 which is encoded by exon 1, 3 or 4.

The endodomain of one CAR may comprise a co-stimulatory domain and an ITAM-containing domain; and the endodomain of the other CAR may comprise a TNF receptor family domain and an ITAM-containing domain.

For example, one CAR (which may be CD19 or CD22-specific) may have the structure:

AgB1-spacer1-TM1-costim-ITAM in which:
AgB1 is the antigen-binding domain;
spacer 1 is the spacer;
TM1 is the transmembrane domain;
costim is a co-stimulatory domain; and
ITAM is an ITAM-containing endodomain;
and the other CAR (which may be CD22 or CD19-specific) may have the structure:

AgB2-spacer2-TM2-TNF-ITAM in which:
AgB2 is the antigen-binding domain;
spacer 2 is the spacer;
TM2 is the transmembrane domain;
TNF is a TNF receptor endodomain; and
ITAM is an ITAM-containing endodomain.

In a second aspect, the present invention provides, a nucleic acid sequence encoding both the first and second chimeric antigen receptors (CARs) as defined in the first aspect of the invention.

The nucleic acid sequence may have the following structure:

AgB1-spacer1-TM1-coexpr-AbB2-spacer2-TM2 in which
AgB1 is a nucleic acid sequence encoding the antigen-binding domain of the first CAR; spacer 1 is a nucleic acid sequence encoding the spacer of the first CAR;
TM1 is a nucleic acid sequence encoding the transmembrane domain of the first CAR; coexpr is a nucleic acid sequence enabling co-expression of both CARs
AgB2 is a nucleic acid sequence encoding the antigen-binding domain of the second CAR; spacer 2 is a nucleic acid sequence encoding the spacer of the second CAR;
TM2 is a nucleic acid sequence encoding the transmembrane domain of the second CAR; which nucleic acid sequence, when expressed in a T cell, encodes a polypeptide which is cleaved at the cleavage site such that the first and second CARs are co-expressed at the T cell surface.

The nucleic acid sequence may have the following structure:

AgB1-spacer1-TM1-endo1-coexpr-AbB2-spacer2-TM2-endo2 in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
endo 1 is a nucleic acid sequence encoding the endodomain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
endo 2 is a nucleic acid sequence encoding the endodomain of the second CAR;
which nucleic acid sequence, when expressed in a T cell, encodes a polypeptide which is cleaved at the cleavage site such that the first and second CARs are co-expressed at the T cell surface.

The nucleic acid sequence allowing co-expression of two CARs may encode a self-cleaving peptide or a sequence which allows alternative means of co-expressing two CARs such as an internal ribosome entry sequence or a $2^{nd}$ promoter or other such means whereby one skilled in the art can express two proteins from the same vector.

Alternative codons may be used in regions of sequence encoding the same or similar amino acid sequences, such as the transmembrane and/or intracellular T cell signalling domain (endodomain) in order to avoid homologous recombination. For example, alternative codons may be used in the portions of sequence encoding the spacer, the transmembrane domain and/or all or part of the endodomain, such that the two CARs have the same or similar amino acid sequences for this or these part(s) but are encoded by different nucleic acid sequences.

In a third aspect, the present invention provides kit which comprises
(i) a first nucleic acid sequence encoding the first chimeric antigen receptor (CAR), which nucleic acid sequence has the following structure:

AgB1-spacer1-TM1 in which

AgB1 is a nucleic acid sequence encoding the antigen-binding domain of the first CAR;

spacer 1 is a nucleic acid sequence encoding the spacer of the first CAR;

TM1 is a nucleic acid sequence encoding the transmembrane domain of the first CAR; and (ii) a second nucleic acid sequence encoding the second chimeric antigen receptor, which nucleic acid sequence has the following structure:

AgB2-spacer2-TM2

AgB2 is a nucleic acid sequence encoding the antigen-binding domain of the second CAR; spacer 2 is a nucleic acid sequence encoding the spacer of the second CAR; and TM2 is a nucleic acid sequence encoding the transmembrane domain of the second CAR.

The kit may comprise (i) a first nucleic acid sequence encoding the first chimeric antigen receptor (CAR), which nucleic acid sequence has the following structure:

AgB1-spacer1-TM1-endo1 in which

AgB1 is a nucleic acid sequence encoding the antigen-binding domain of the first CAR;

spacer 1 is a nucleic acid sequence encoding the spacer of the first CAR;

TM1 is a nucleic acid sequence encoding the transmembrane domain of the first CAR;

endo 1 is a nucleic acid sequence encoding the endodomain of the first CAR; and (ii) a second nucleic acid sequence encoding the second chimeric antigen receptor (CAR), which nucleic acid sequence has the following structure:

AgB2-spacer2-TM2-endo2

AgB2 is a nucleic acid sequence encoding the antigen-binding domain of the second CAR;

spacer 2 is a nucleic acid sequence encoding the spacer of the second CAR;

TM2 is a nucleic acid sequence encoding the transmembrane domain of the second CAR;

endo 2 is a nucleic acid sequence encoding the endodomain of the second CAR.

In a fourth aspect, the present invention provides a kit comprising: a first vector which comprises the first nucleic acid sequence; and a second vector which comprises the second nucleic acid sequence.

The vectors may be plasmid vectors, retroviral vectors or transposon vectors. The vectors may be lentiviral vectors.

In a fifth aspect, the present invention provides a vector comprising a nucleic acid sequence according to the second aspect of the invention. The vector may be a lentiviral vector.

The vector may be a plasmid vector, a retroviral vector or a transposon vector.

In a sixth aspect the present invention provides a method for making a cell according to the first aspect of the invention, which comprises the step of introducing one or more nucleic acid sequence(s) encoding the first and second CARs; or one or more vector(s), as defined above, into a T cell.

The cell may be from a sample isolated from a patient, a related or unrelated haematopoietic transplant donor, a completely unconnected donor, from cord blood, differentiated from an embryonic cell line, differentiated from an inducible progenitor cell line, or derived from a transformed cell line.

In a seventh aspect, the present invention provides a pharmaceutical composition comprising a plurality of cells according to the first aspect of the invention.

In an eighth aspect the present invention provides a method for treating and/or preventing a disease, which comprises the step of administering a pharmaceutical composition according to the seventh aspect of the invention to a subject.

The method may comprise the following steps:

(i) isolation of a cell-containing sample from a subject;

(ii) transduction or transfection of the cells with one or more nucleic acid sequence(s) encoding the first and second CAR or one or more vector(s) comprising such nucleic acid sequence(s); and (iii) administering the cells from (ii) to the subject.

The disease may be cancer. The cancer may be a B cell malignancy.

In a ninth aspect the present invention provides a pharmaceutical composition according to the seventh aspect of the invention for use in treating and/or preventing a disease.

In a tenth aspect the present invention provides the use of a cell according to the first aspect of the invention in the manufacture of a medicament for treating and/or preventing a disease.

The present invention also provides a nucleic acid sequence which comprises:

a) a first nucleotide sequence encoding a first chimeric antigen receptor (CAR);

b) a second nucleotide sequence encoding a second CAR; wherein one CAR binds CD19 and the other CAR binds CD22; and c) a sequence encoding a self-cleaving peptide positioned between the first and second nucleotide sequences, such that the two CARs are expressed as separate entities.

Alternative codons may be used in one or more portion(s) of the first and second nucleotide sequences in regions which encode the same or similar amino acid sequence(s).

The present invention also provides a vector and a cell comprising such a nucleic acid.

The present inventors have also developed new anti-CD19 and anti-CD22 CARs with improved properties.

Thus in an eleventh aspect, the present invention provides a chimeric antigen receptor (CAR) comprising a CD19-binding domain which comprises a) a heavy chain variable region (VH) having complementarity determining regions (CDRs) with the following sequences:

```
CDR1 - SYWMN;              (SEQ ID No. 15)
CDR2 - QIWPGDGDTNYNGKFK    (SEQ ID No. 16)
CDR3 - RETTTVGRYYYAMDY;    (SEQ ID No. 17)
``` and b) a light chain variable region (VL) having CDRs with the following sequences:

```
CDR1 - KASQSVDYDGDSYLN;    (SEQ ID No. 18)
CDR2 - DASNLVS             (SEQ ID No. 19)
CDR3 - QQSTEDPWT.          (SEQ ID No. 20)
```

The CD19 binding domain may comprise a VH domain having the sequence shown as SEQ ID No. 23, or SEQ ID NO 24; or a VL domain having the sequence shown as SEQ ID No 25, SEQ ID No. 26 or SEQ ID No. 40 or a variant thereof having at least 90% sequence identity which retains the capacity to bind CD19.

The CD19 binding domain may comprise the sequence shown as SEQ ID No 21, SEQ ID No. 22 or SEQ ID No. 39 or a variant thereof having at least 90% sequence identity which retains the capacity to bind CD19.

In a twelfth aspect the present invention provides a chimeric antigen receptor (CAR) comprising a CD22-binding domain which comprises a) a heavy chain variable region (VH) having complementarity determining regions (CDRs) with the following sequences:

```
CDR1 - NYWIN;              (SEQ ID No. 27)
CDR2 - NIYPSDSFTNYNQKFKD   (SEQ ID No. 28)
CDR3 - DTQERSWYFDV;        (SEQ ID No. 29)
``` and b) a light chain variable region (VL) having CDRs with the following sequences:

```
CDR1 - RSSQSLVHSNGNTYLH;   (SEQ ID No. 30)
CDR2 - KVSNRFS             (SEQ ID No. 31)
CDR3 - SQSTHVPWT.          (SEQ ID No. 32)
```

The CD22 binding domain may comprise a VH domain having the sequence shown as SEQ ID No. 35, or SEQ ID NO 36; or a VL domain having the sequence shown as SEQ ID No 37, or SEQ ID No. 38 or a variant thereof having at least 90% sequence identity which retains the capacity to bind CD22.

The CD22 binding domain may comprise the sequence shown as SEQ ID No 33 or SEQ ID No. 34 or a variant thereof having at least 90% sequence identity which retains the capacity to bind CD22.

In a thirteenth aspect there is provided a cell which expresses a chimeric antigen receptor according to the eleventh aspect of the invention or a chimeric antigen receptor according to the twelfth aspect of the invention at the cell surface.

In a fourteenth aspect, there is provided a nucleic acid sequence encoding a chimeric antigen receptor according to the eleventh aspect of the invention or a chimeric antigen receptor according to the twelfth aspect of the invention.

In a fifteenth aspect, the present invention provides a vector comprising a nucleic acid sequence according to the fourteenth aspect of the invention. The vector may be a lentiviral vector.

The vector may be a plasmid vector, a retroviral vector or a transposon vector.

In a sixteenth aspect, the present invention provides a method for making a cell according to the thirteenth aspect of the invention, which comprises the step of introducing one or more nucleic acid sequence(s); or one or more vector(s), as defined above, into a cell.

The cell may be a T-cell or a natural killer (NK) cell. The cell may be from a sample isolated from a patient, a related or unrelated haematopoietic transplant donor, a completely unconnected donor, from cord blood, differentiated from an embryonic cell line, differentiated from an inducible progenitor cell line, or derived from a transformed cell line.

In a seventeenth aspect, the present invention provides a pharmaceutical composition comprising a plurality of cells according to the thirteenth aspect of the invention.

In an eighteenth aspect the present invention provides a method for treating and/or preventing a disease, which comprises the step of administering a pharmaceutical composition according to the seventeenth aspect of the invention to a subject.

The method may comprise the following steps:
(i) isolation of a cell-containing sample from a subject;
(ii) transduction or transfection of the cells with a nucleic acid sequence encoding the CAR or a vector comprising such a nucleic acid sequence; and
(iii) administering the cells from (ii) to a the subject.

The disease may be cancer. The cancer may be a B cell malignancy.

In a nineteenth aspect the present invention provides a pharmaceutical composition according to the seventeenth aspect of the invention for use in treating and/or preventing a disease.

In a twentieth aspect the present invention provides the use of a cell according to the thirteenth aspect of the invention in the manufacture of a medicament for treating and/or preventing a disease.

There is also provided a cell according to the first aspect of the invention, which comprises a first CAR as defined in the eleventh aspect of the invention and a second CAR as defined in the twelfth aspect of the invention.

There is also provided a nucleic acid sequence according to the second aspect of the invention, encoding a first CAR as defined in the eleventh aspect of the invention and a second CAR as defined in the twelfth aspect of the invention.

There is also provided a kit according to the third aspect of the invention, wherein the first nucleic acid sequence encodes a first CAR as defined in the eleventh aspect of the invention and the second nucleic acid sequence encodes a second CAR as defined in the twelfth aspect of the invention.

There is also provided a vector according to the fifth aspect of the invention, which comprises a nucleic acid sequence encoding a first CAR as defined in the eleventh aspect of the invention and a second CAR as defined in the twelfth aspect of the invention.

The present inventors have also found that, in an OR gate system, performance is improved if the co-stimulatory domain and domain producing survival signals are "split" between the two (or more) CARs.

Thus, in a twenty-first aspect there is provided a cell which co-expresses a first chimeric antigen receptor (CAR) and second CAR at the cell surface, each CAR comprising an intracellular signalling domain, wherein the intracellular signalling domain of the first CAR comprises a co-stimulatory domain; and the intracellular signalling domain of the second CAR comprises a TNF receptor family endodomain.

The co-stimulatory domain may be a CD28 co-stimulatory domain.

The TNF receptor family endodomain may be, for example OX-40 or 4-1 BB endodomain.

The intracellular signalling domain of the first and the second CAR may also comprise an ITAM-containing domain, such as a CD3 zeta endodomain.

The first CAR may have the structure:

AgB1-spacer1-TM1-costim-ITAM in which:
AgB1 is the antigen-binding domain of the first CAR;
spacer 1 is the spacer of the first CAR;
TM1 is the transmembrane domain of the first CAR;
costim is a co-stimulatory domain; and
ITAM is an ITAM-containing endodomain.
The second CAR may have the structure:

AgB2-spacer2-TM2-TNF-ITAM in which:
AgB2 is the antigen-binding domain of the second CAR;
spacer 2 is the spacer of the second CAR;
TM2 is the transmembrane domain of the second CAR;
TNF is a TNF receptor endodomain; and
ITAM is an ITAM-containing endodomain.

One CAR out of the first and second CAR may target CD19 and the other CAR may target CD22.

In a twenty-second aspect there is provided a nucleic acid sequence encoding both the first and second chimeric antigen receptors (CARs) as defined in the twenty-first aspect of the invention.

The nucleic acid sequence may have the following structure:

AgB1-spacer1-TM1-costim-ITAM1-coexpr-AbB2-spacer2-TM2-TNF-ITAM2 in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
costim is a nucleic acid sequence encoding a co-stimulatory domain;
ITAM1 is a nucleic acid sequence encoding the ITAM-containing endodomain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
TNF is a nucleic acid sequence encoding a TNF receptor endodomain;
ITAM2 is a nucleic acid sequence encoding the ITAM-containing endodomain of the second CAR.

When the nucleic acid sequence is expressed in a cell it may encode a polypeptide which is cleaved at the cleavage site such that the first and second CARs are co-expressed at the cell surface.

In a twenty-third aspect, there is provided a kit which comprises
(i) a first nucleic acid sequence encoding the first chimeric antigen receptor (CAR) as defined in the twenty-first aspect of the invention, which nucleic acid sequence has the following structure:

AgB1-spacer1-TM1-costim-ITAM1 in which
AgB1 is a nucleic acid sequence encoding the antigen-binding domain of the first CAR;
spacer 1 is a nucleic acid sequence encoding the spacer of the first CAR;

TM1 is a nucleic acid sequence encoding the transmembrane domain of the first CAR;
costim is a nucleic acid sequence encoding a co-stimulatory domain;
ITAM1 is a nucleic acid sequence encoding the ITAM-containing endodomain of the first CAR;
and
(ii) a second nucleic acid sequence encoding the second chimeric antigen receptor (CAR) as defined in the twenty-first aspect of the invention, which nucleic acid sequence has the following structure:

AbB2-spacer2-TM2-TNF-ITAM2

AgB2 is a nucleic acid sequence encoding the antigen-binding domain of the second CAR; spacer 2 is a nucleic acid sequence encoding the spacer of the second CAR;
TM2 is a nucleic acid sequence encoding the transmembrane domain of the second CAR;
TNF is a nucleic acid sequence encoding a TNF receptor endodomain; and
ITAM2 is a nucleic acid sequence encoding the ITAM-containing endodomain of the second CAR.

In a twenty-fourth aspect there is provided a vector comprising a nucleic acid sequence according to the twenty-second aspect of the invention or as defined in the twenty-third aspect of the invention.

In a twenty-fifth aspect, there is provided a method for making a cell according to the twenty-first aspect of the invention, which comprises the step of introducing: a nucleic acid sequence according to twenty-second aspect of the invention; a first nucleic acid sequence and a second nucleic acid sequence as defined in the twenty-third aspect of the invention; or a vector according to the twenty-fourth aspect of the invention, into a cell.

In a twenty-sixth aspect, the present invention provides a pharmaceutical composition comprising a plurality of cells according to the twenty-first aspect of the invention.

There is also provided a method for treating and/or preventing a disease, which comprises the step of administering a pharmaceutical composition according to the twenty-sixth aspect of the invention to a subject.

There is also provided a pharmaceutical composition according to the twenty-sixth aspect of the invention for use in treating and/or preventing a disease.

There is also provided the use of a cell according to the twenty-first aspect of the invention in the manufacture of a medicament for treating and/or preventing a disease.

By providing one CAR which targets CD19 and one CAR which targets CD22, it is possible to target each of these markers, thereby reducing the problem of cancer escape.

Because the CARs are expressed on the surface of the cell as separate molecules, this approach overcomes the spatial and accessibility issues associated with TanCARs. Cell activation efficiency is also improved. If each CAR has its own spacer, it is possible to tailor the spacer and therefore the distance that the binding domain projects from the cell surface and its flexibility etc. to the particular target antigen. This choice is unfettered by the design considerations associated with TanCARs, i.e. that one CAR needs to be juxtaposed to the T cell membrane and one CAR needs to be distal, positioned in tandem to the first CAR.

By providing a single nucleic acid which encodes the two CARs separated by a cleavage site, it is possible to engineer cells to co-express the two CARs using a simple single transduction procedure. A double transfection procedure could be used with CAR-encoding sequences in separate constructs, but this would be more complex and expensive and requires more integration sites for the nucleic acids. A double transfection procedure would also be associated with uncertainty as to whether both CAR-encoding nucleic acids had been transduced and expressed effectively.

The CARs will have portions of high homology, for example the transmembrane and/or intracellular signalling domains are likely to be highly homologous. If the same or similar linkers are used for the two CARs, then they will also be highly homologous. This would suggest that an approach where both CARs are provided on a single nucleic acid sequence would be inappropriate, because of the likelihood of homologous recombination between the sequences. However, the present inventors have found that by "codon wobbling" the portions of sequence encoding areas of high homology, it is possible to express two CARs from a single construct with high efficiency. Codon wobbling involves using alternative codons in regions of sequence encoding the same or similar amino acid sequences.

DESCRIPTION OF THE FIGURES

FIG. 1A) Schematic diagram illustrating a classical CAR. FIG. 1B-1D: Different generations and permutations of CAR endodomains: (FIG. 1B) initial designs transmitted ITAM signals alone through FccR1-γ or CD3ζ endodomain, while later designs transmitted additional (FIG. 1C) one or (FIG. 1D) two co-stimulatory signals in the same compound endodomain.

(FIG. 3A) an OR gate cassette is constructed so that both CARs are co-expressed using a FMD-2A peptide. Any homologous sequences are codon-wobbled to avoid recombination. (FIG. 3B) The two CARs are co-expressed as separate proteins on the T-cell surface.

FIG. 4: Example of codon-wobbling to allow co-expression in a retroviral vector of identical peptide sequences but avoiding homologous recombination. Here, wild-type HCH2CH3-CD28tmZeta (SEQ ID NO: 48) is aligned with codon-wobbled HCH2CH3-CD28tmZeta (SEQ ID NO: 49).

FIGS. 5A-5C: Demonstrating functionality of anti-CD19 OR CD22 CAR gate. (FIG. 5A) Cartoon of construct: S1—signal peptide 1; HA—haemagglutin tag; HCH2CH3—hinge, CH2CH3 of IgG1 wild-type sequence; CD28tmZ—CD28 transmembrane domain and CD3 Zeta wobbled sequence; 2A—Foot and mouth disease 2A peptide; S2—signal peptide 2; V5—v5 epitope tag; aCD22—anti-CD22 scFv; HCH2CH3'—hinge, CH2CH3 of IgG1 wobbled sequence; CD28tmZ—CD28 transmembrane domain and CD3 Zeta wobbled sequence; (FIG. 5B) Co-expression of two receptors from a single vector. Peripheral blood T-cells were transduced with bicistronic vector after stimulation with OKT3 and anti-CD28. Cells were analysed five days after transduction by staining with anti-V5-FITC (invitrogen) and anti-HA-PE (abCam). The two CARs can be detected simultaneously on the T-cell surface. (FIG. 5C) Non-transduced T-cells, T-cells expressing just anti-CD19 CAR, T-cells expressing just anti-CD22 CAR and T-cells expressing the anti-CD19 OR CD22 CAR gate were challenged with target cells expressing neither CD19 or CD22, either CD19 or CD22 singly, or both antigen. T-cells expressing the anti-CD19 OR CD22 CAR gate could kill target cells even if one antigen was absent.

FIG. 8: Comparison of the binding kinetics between soluble scFv-CD19 binding for CD19ALAb scFv and fmc63 scFv

FIG. 11A) Killing assay of CD22 positive target cells comparing a CAR with a CD22ALAb antigen binding domain and an equivalent CAR with an M971 binding domain. FIG. 11B) Assay comparing IFNγ release following co-culture 1:1 with CD22 positive SupT1 cells

FIG. 13A: CD19 and CD22 CAR both have 41BB-CD3zeta compound endodomains; FIG. 13B: CD19 and CD22 CAR both have OX40-CD3zeta compound endodomains; FIG. 13C: CD19 CAR has 41BB-CD3zeta compound endodomain and CD22 CAR has CD28-CD3zeta compound endodomain; and FIG. 13D: CD19 CAR has OX40-CD3zeta compound endodomain and CD22 CAR has CD28-CD3zeta compound endodomain.

DETAILED DESCRIPTION

Chimeric Antigen Receptors (CARs)

Figure 1:
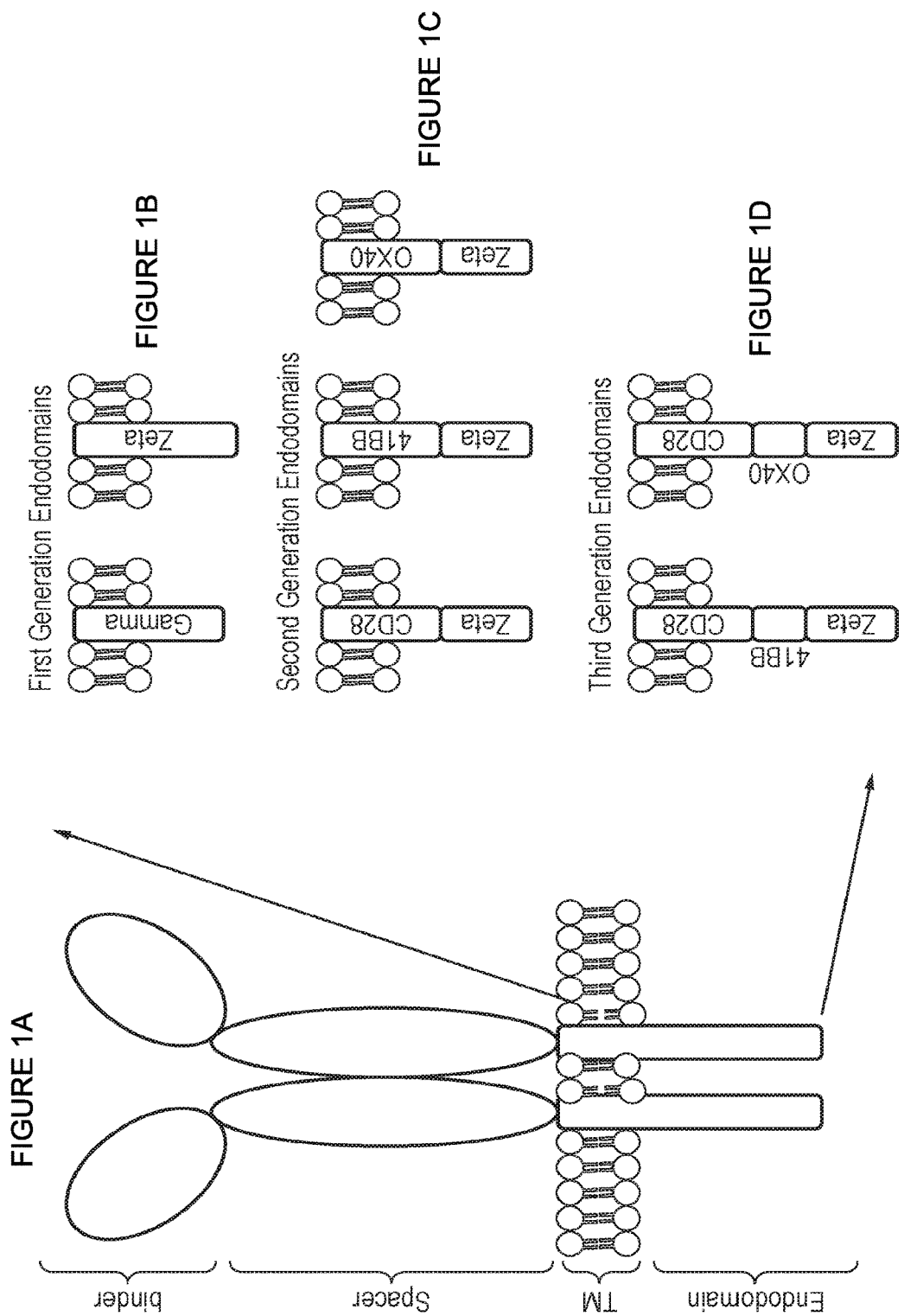
FIGS. 1A-1D.

CARs, which are shown schematically in FIGS. 1A-1D, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FccR1 or CD3. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3 results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

The first aspect of the invention relates to a cell which co-expresses a first CAR and a second CAR, wherein one CAR binds CD19 and the other CAR binds CD22, such that a T-cell can recognize a target cells expressing either of these markers.

Thus, the antigen binding domains of the first and second CARs of the present invention bind to different antigens and both CARs may comprise an activating endodomain. The two CARs may comprise spacer domains which may be the same, or sufficiently different to prevent cross-pairing of the two different receptors. A cell can hence be engineered to activate upon recognition of either or both CD19 and CD22. This is useful in the field of oncology as indicated by the Goldie-Coldman hypothesis: sole targeting of a single antigen may result in tumour escape by modulation of said antigen due to the high mutation rate inherent in most cancers. By simultaneously targeting two antigens, the probably of such escape is exponentially reduced.

It is important that the two CARs do not heterodimerize.

The first and second CAR of the T cell of the present invention may be produced as a polypeptide comprising both CARs, together with a cleavage site.

Signal Peptide

The CARs of the cell of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID No. 1, 2 or 3 or a variant thereof having 5, 4, 3, 2 or 1 amino acid mutations (insertions, substitutions or additions) provided that the signal peptide still functions to cause cell surface expression of the CAR.

SEQ ID No. 1:     MGTSLLCWMALCLLGADHADG

The signal peptide of SEQ ID No. 1 is compact and highly efficient. It is predicted to give about 95% cleavage after the terminal glycine, giving efficient removal by signal peptidase.

SEQ ID No. 2:     MSLPVTALLLPLALLLHAARP

The signal peptide of SEQ ID No. 2 is derived from IgG1.

SEQ ID No. 3:     MAVPTQVLGLLLLWLTDARC

The signal peptide of SEQ ID No. 3 is derived from CD8.

The signal peptide for the first CAR may have a different sequence from the signal peptide of the second CAR.

CD19

Figure 12:
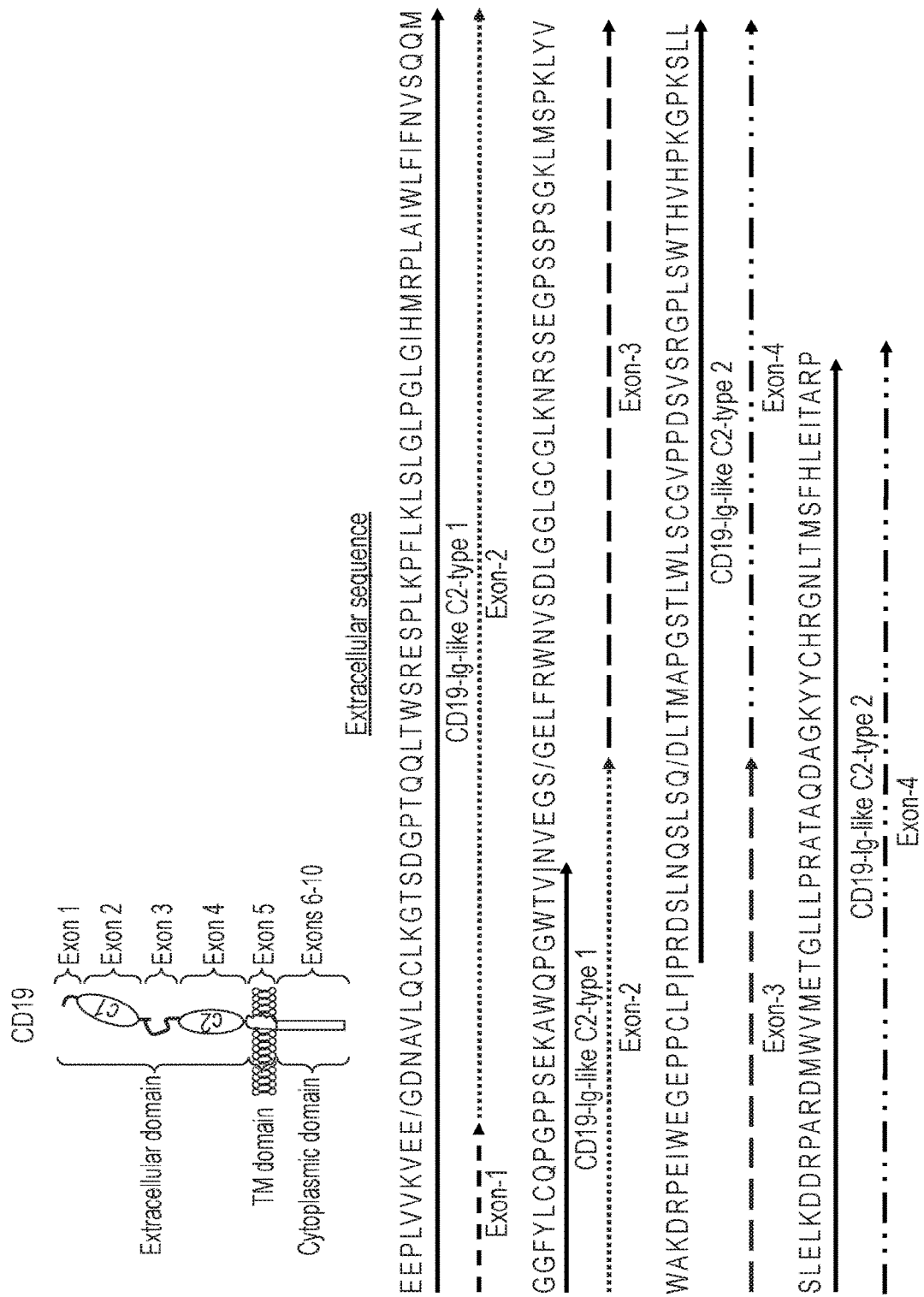
FIG. 12: CD19 structure and exons (SEQ ID NO: 46).
Figure 13A:
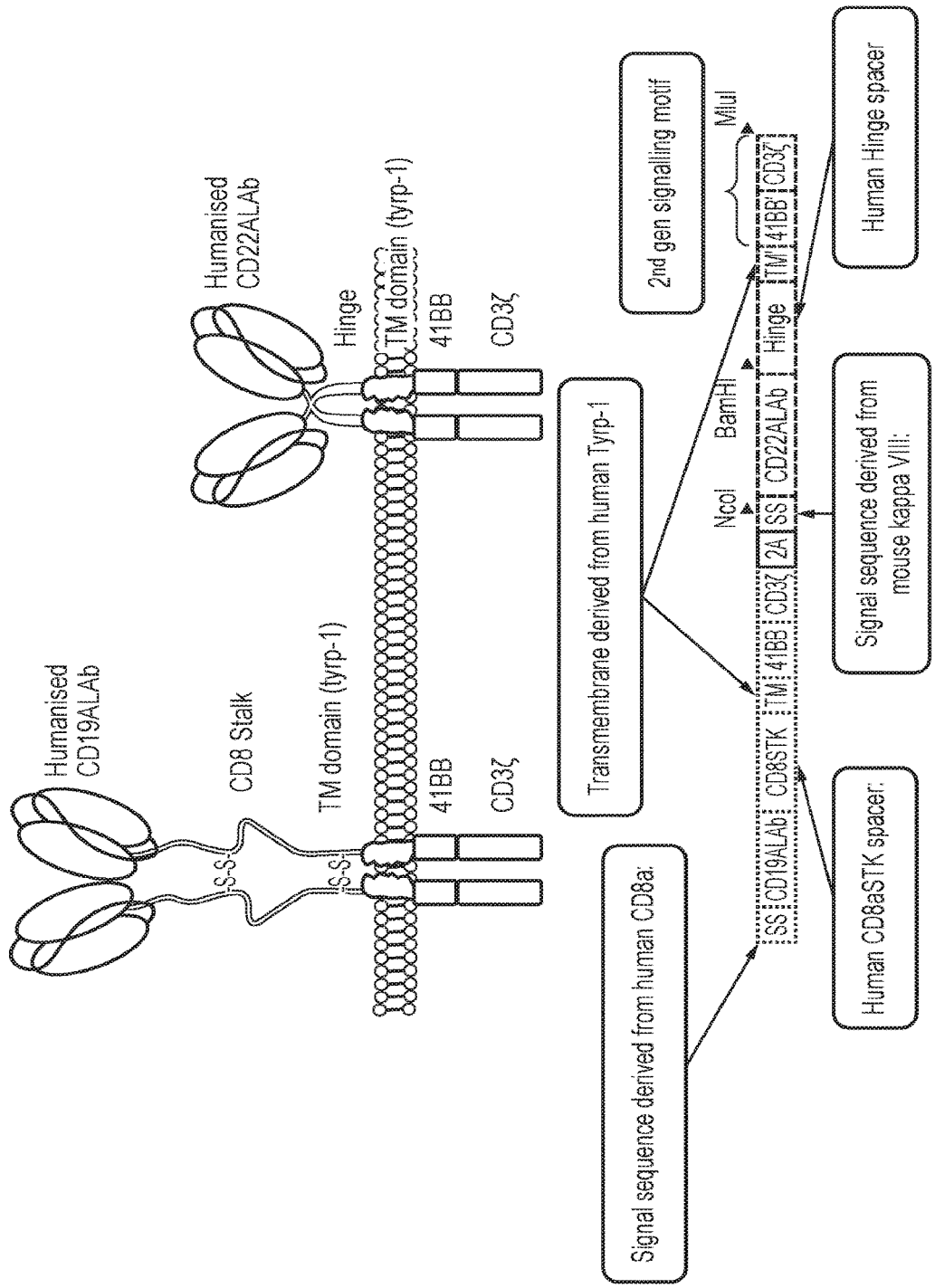
FIGS. 13A-13D: Schematic diagrams and construct maps illustrating the four constructs tested in Example 5. In the construct map, portions marked with are codon-wobbled.
Figure 13B:
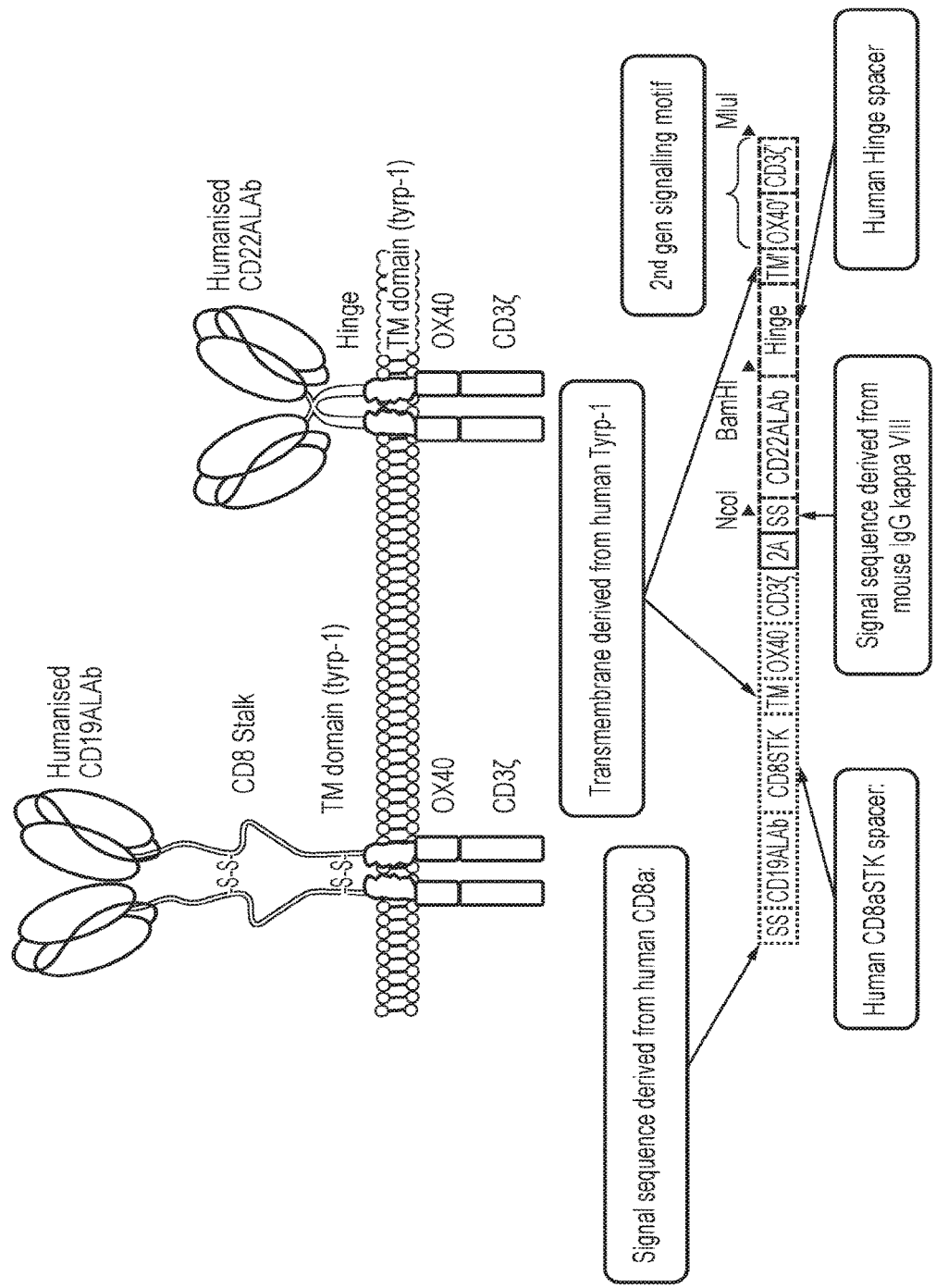
Figure 13C:
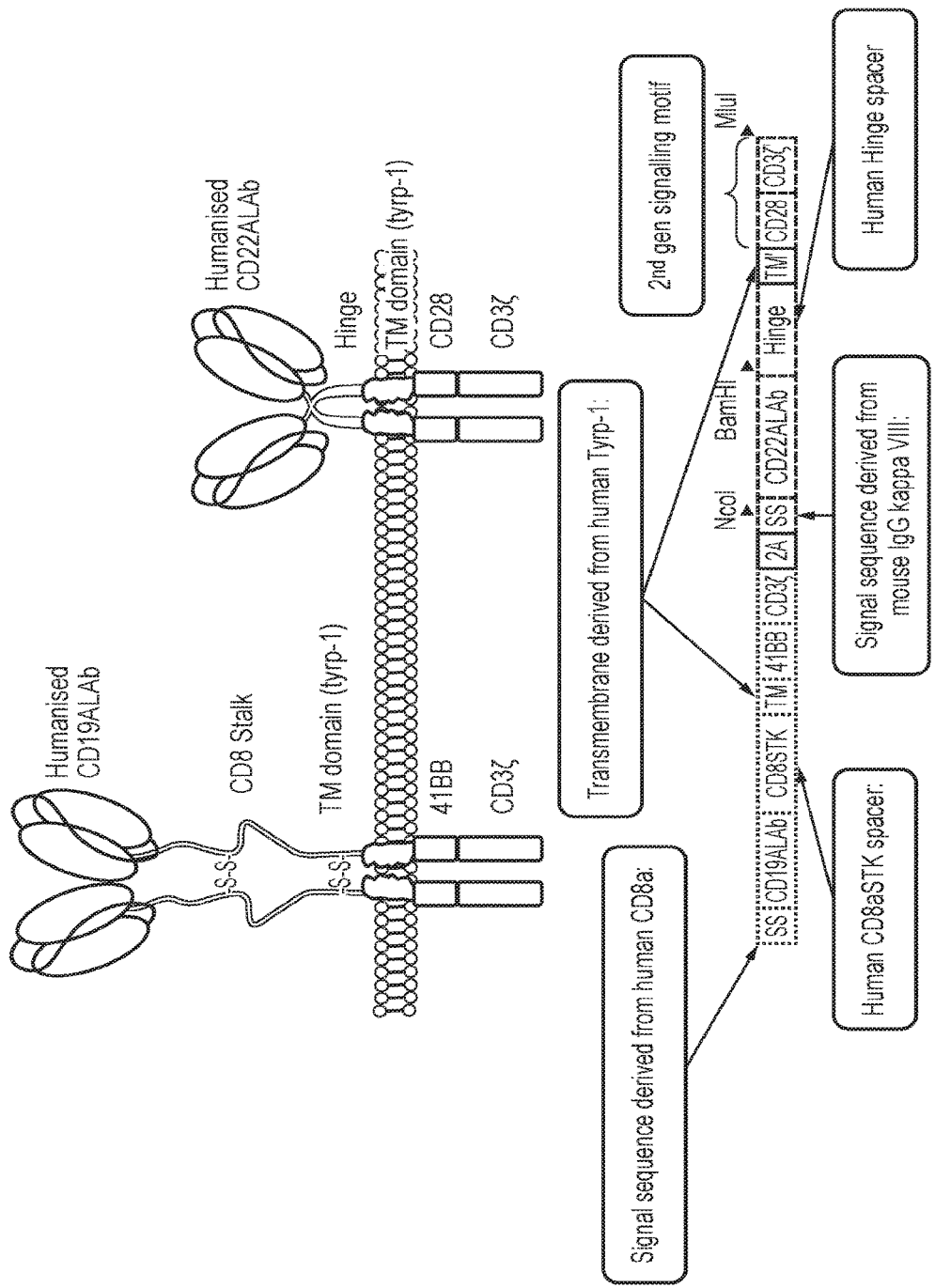
Figure 13D:
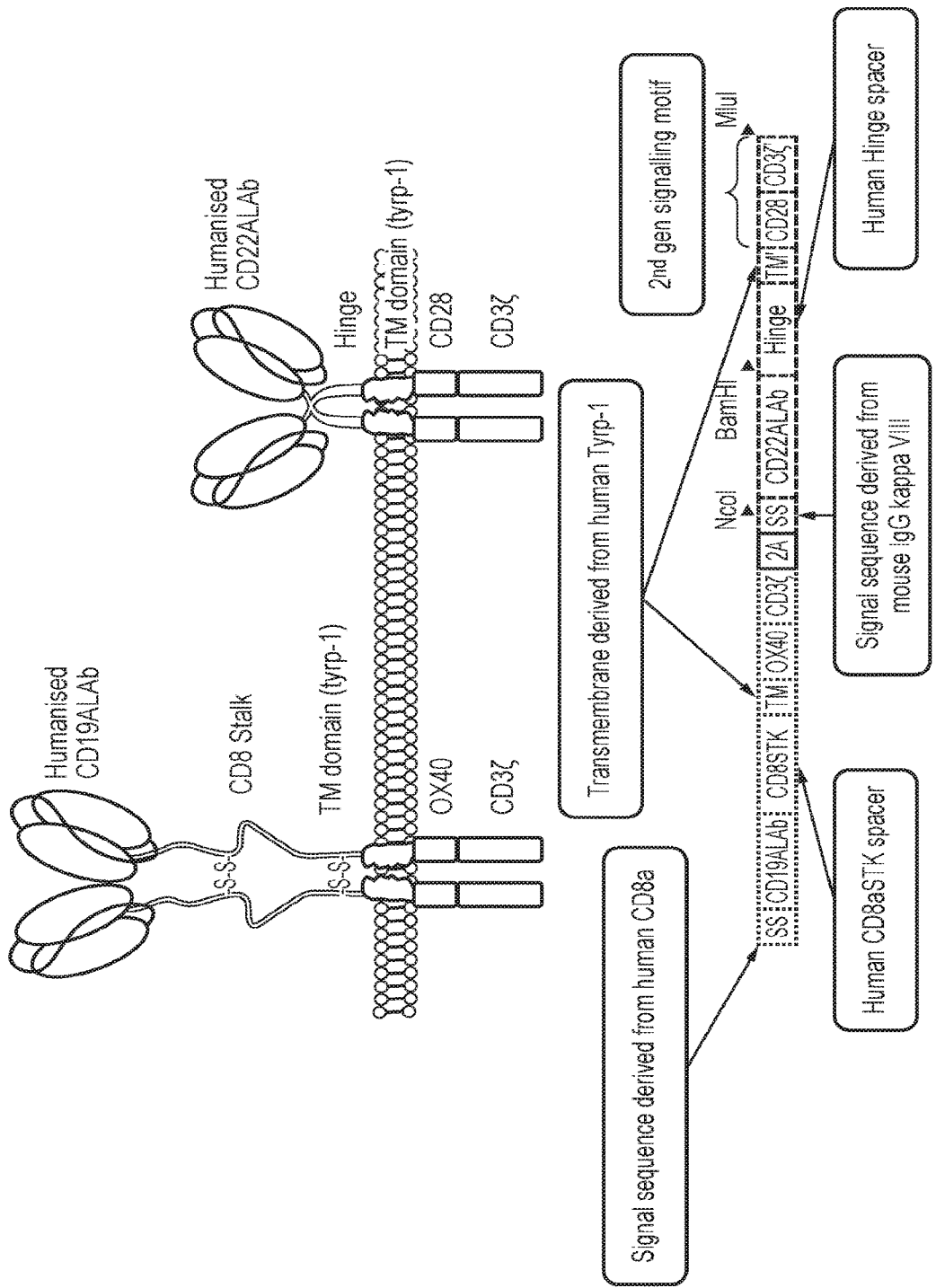

The human CD19 antigen is a 95 kd transmembrane glycoprotein belonging to the immunoglobulin superfamily. CD19 is classified as a type I transmembrane protein, with a single transmembrane domain, a cytoplasmic C-terminus, and extracellular N-terminus. The general structure for CD19 is illustrated in FIG. 12.

CD19 is a biomarker for normal and neoplastic B cells, as well as follicular dendritic cells. In fact, it is present on B cells from earliest recognizable B-lineage cells during development to B-cell blasts but is lost on maturation to plasma cells. It primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. CD19 is expressed very early in B-cell differentiation and is only lost at terminal B-cell differentiation into plasma cells. Consequently, CD19 is expressed on all B-cell malignancies apart from multiple myeloma.

Different designs of CARs have been tested against CD19 in different centres, as outlined in the following Table:

TABLE 1

| Centre | Binder | Endodomain | Comment |
| --- | --- | --- | --- |
| University College London | Fmc63 | CD3-Zeta | Low-level brief persistence |
| Memorial Sloane Kettering | SJ25C1 | CD28-Zeta | Short-term persistence |
| NCI/KITE | Fmc63 | CD28-Zeta | Long-term low-level persistence |
| Baylor, Centre for Cell and Gene Therapy | Fmc63 | CD3-Zeta/ CD28-Zeta | Short-term low-level persistence |
| UPENN/Novartis | Fmc63 | 41BB-Zeta | Long-term high-level persistence |

As shown above, most of the studies conducted to date have used an scFv derived from the hybridoma fmc63 as part of the binding domain to recognize CD19.

As shown in FIG. 12, the gene encoding CD19 comprises ten exons: exons 1 to 4 encode the extracellular domain; exon 5 encodes the transmembrane domain; and exons 6 to 10 encode the cytoplasmic domain, In the CD19/CD22 OR gate of the present invention, the antigen-binding domain of the anti-CD19 CAR may bind an epitope of CD19 encoded by exon 1 of the CD19 gene.

In the CD19/CD22 OR gate of the present invention, the antigen-binding domain of the anti-CD19 CAR may bind an epitope of CD19 encoded by exon 3 of the CD19 gene.

In the CD19/CD22 OR gate of the present invention, the antigen-binding domain of the anti-CD19 CAR may bind an epitope of CD19 encoded by exon 4 of the CD19 gene.

CD19ALAb

The present inventors have developed a new anti-CD19 CAR which has improved properties compared to a known anti-CD19 CAR which comprises the binder fmc63 (see Examples 2 and 3). The antigen binding domain of the CAR is based on the CD19 binder CD19ALAb, which has the CDRs and VH/VL regions identified below.

The present invention therefore also provides a CAR which comprises a CD19-binding domain which comprises
a) a heavy chain variable region (VH) having complementarity determining regions (CDRs) with the following sequences:

```
CDR1 - SYWMN;              (SEQ ID No. 15)
CDR2 - QIWPGDGDTNYNGKFK    (SEQ ID No. 16)
CDR3 - RETTTVGRYYYAMDY;    (SEQ ID No. 17)
``` and
b) a light chain variable region (VL) having CDRs with the following sequences:

```
CDR1 - KASQSVDYDGDSYLN;    (SEQ ID No. 18)
CDR2 - DASNLVS              (SEQ ID No. 19)
CDR3 - QQSTEDPWT.           (SEQ ID No. 20)
```

It may be possible to introduce one or more mutations (substitutions, additions or deletions) into the or each CDR without negatively affecting CD19-binding activity. Each CDR may, for example, have one, two or three amino acid mutations.

The CAR of the present invention may comprise one of the following amino acid sequences:

```
(Murine CD19ALAb scFv sequence)
                                      SEQ ID No. 21
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSSDIQLTQSPASLAVSLGQRATISCKAS

QSVDYDGDSYLNWYQQIPGQPPKLLIYDASNLVSGIPPRFSGSGSGTDFT

LNIHPVEKVDAATYHCQQSTEDPWTFGGGTKLEIK (Humanised CD19ALAb scFv sequence - Heavy 19,
Kappa 16)
                                      SEQ ID No. 22
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSSDIQLTQSPDSLAVSLGERATINCKAS

QSVDYDGDSYLNWYQQKPGQPPKLLIYDASNLVSGVPDRFSGSGSGTDFT

LTISSLQAADVAVYHCQQSTEDPWTFGQGTKVEIKR (Humanised CD19ALAb scFv sequence - Heavy 19,
Kappa 7)
                                      SEQ ID No. 39
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSSDIQLTQSPDSLAVSLGERATINCKAS

QSVDYDGDSYLNWYQQKPGQPPKVLIYDASNLVSGVPDRFSGSGSGTDFT

LTISSLQAADVAVYYCQQSTEDPWTFGQGTKVEIKR
```

The scFv may be in a VH-VL orientation (as shown in SEQ ID No.s 21, 22 and 39) or a VL-VH orientation.

The CAR of the present invention may comprise one of the following VH sequences:

```
(Murine CD19ALAb VH sequence)
                                      SEQ ID No. 23
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSS (Humanised CD19ALAb VH sequence)
                                      SEQ ID No. 24
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSS
```

The CAR of the present invention may comprise one of the following VL sequences:

```
(Murine CD19ALAb VL sequence)
                                      SEQ ID No. 25
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIK (Humanised CD19ALAb VL sequence, Kappa 16)
                                      SEQ ID No. 26
DIQLTQSPDSLAVSLGERATINCKASQSVDYDGDSYLNWYQQKPGQPPKL

LIYDASNLVSGVPDRFSGSGSGTDFTLTISSLQAADVAVYHCQQSTEDPW

TFGQGTKVEIKR (Humanised CD19ALAb VL sequence, Kappa 7)
                                      SEQ ID No. 40
DIQLTQSPDSLAVSLGERATINCKASQSVDYDGDSYLNWYQQKPGQPPKV

LIYDASNLVSGVPDRFSGSGSGTDFTLTISSLQAADVAVYYCQQSTEDPW

TFGQGTKVEIKR
```

The CAR of the invention may comprise a variant of the sequence shown as SEQ ID No. 21, 22, 23, 24, 25, 26, 39 or 40 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at http://blast.ncbi.nlm.nih.gov.

CD22

The human CD22 antigen is a molecule belonging to the SIGLEC family of lectins. It is found on the surface of mature B cells and on some immature B cells. Generally speaking, CD22 is a regulatory molecule that prevents the overactivation of the immune system and the development of autoimmune diseases.

CD22 is a sugar binding transmembrane protein, which specifically binds sialic acid with an immunoglobulin (Ig) domain located at its N-terminus. The presence of Ig domains makes CD22 a member of the immunoglobulin superfamily. CD22 functions as an inhibitory receptor for B cell receptor (BCR) signaling.

CD22 is a molecule of the IgSF which may exist in two isoforms, one with seven domains and an intra-cytoplasmic tail comprising of three ITIMs (immune receptor tyrosine-based inhibitory motifs) and an ITAM; and a splicing variant which instead comprises of five extracellular domains and an intra-cytoplasmic tail carrying one ITIM. CD22 is thought to be an inhibitory receptor involved in the control of B-cell responses to antigen. Like CD19, CD22 is widely considered to be a pan-B antigen, although expression on some non-lymphoid tissue has been described. Targeting of CD22 with therapeutic monoclonal antibodies and immunoconjugates has entered clinical testing.

Examples of anti-CD22 CARs are described by Haso et al. (Blood; 2013; 121(7)). Specifically, anti-CD22 CARs with antigen-binding domains derived from m971, HA22 and BL22 scFvs are described.

The antigen-binding domain of the anti-CD22 CAR may bind CD22 with a $K_D$ in the range 30-50 nM, for example 30-40 nM. The $K_D$ may be about 32 nM.

CD-22 has seven extracellular IgG-like domains, which are commonly identified as Ig domain 1 to Ig domain 7, with Ig domain 7 being most proximal to the B cell membrane and Ig domain 7 being the most distal from the Ig cell membrane (see Haso et al 2013 as above FIG. 2B).

The positions of the Ig domains in terms of the amino acid sequence of CD22 (http://www.uniprot.org/uniprot/P20273) are summarised in the following table:

| Ig domain | Amino acids |
| --- | --- |
| 1 | 20-138 |
| 2 | 143-235 |
| 3 | 242-326 |
| 4 | 331-416 |
| 5 | 419-500 |
| 6 | 505-582 |
| 7 | 593-676 |

The antigen-binding domain of the second CAR may bind to a membrane-distal epitope on CD22. The antigen-binding domain of the second CAR may bind to an epitope on Ig domain 1, 2, 3 or 4 of CD22, for example on Ig domain 3 of CD22. The antigen-binding domain of the second CAR may bind to an epitope located between amino acids 20-416 of CD22, for example between amino acids 242-326 of CD22.

The anti-CD22 antibodies HA22 and BL22 (Haso et al 2013 as above) and CD22ALAb, described below, bind to an epitope on Ig domain 3 of CD22.

The antigen binding domain of the second CAR may not bind to a membrane-proximal epitope on CD22. The antigen-binding domain of the second CAR may not bind to an epitope on Ig domain 5, 6 or 7 of CD22. The antigen-binding domain of the second CAR may not bind to an epitope located between amino acids 419-676 of CD22, such as between 505-676 of CD22.

CD22ALAb

The present inventors have developed a new anti-CD22 CAR which has improved properties compared to a known anti-CD22 CAR which comprises the binder m971 (see Examples 2 and 3 and Haso et al (2013) as above). The antigen binding domain of the CAR is based on the CD22 binder CD22ALAb, which has the CDRs and VH/VL regions identified below.

The present invention therefore also provides a CAR which comprises a CD22-binding domain which comprises a) a heavy chain variable region (VH) having complementarity determining regions (CDRs) with the following sequences:

```
CDR1 - NYWIN;              (SEQ ID No. 27)
CDR2 - NIYPSDSFTNYNQKFKD   (SEQ ID No. 28)
CDR3 - DTQERSWYFDV;        (SEQ ID No. 29)
``` and b) a light chain variable region (VL) having CDRs with the following sequences:

```
CDR1 - RSSQSLVHSNGNTYLH;   (SEQ ID No. 30)
CDR2 - KVSNRFS             (SEQ ID No. 31)
CDR3 - SQSTHVPWT.          (SEQ ID No. 32)
```

It may be possible to introduce one or more mutations (substitutions, additions or deletions) into the or each CDR without negatively affecting CD22-binding activity. Each CDR may, for example, have one, two or three amino acid mutations.

The CAR of the present invention may comprise one of the following amino acid sequences:

```
(Murine CD22ALAb scFv sequence)
                                        SEQ ID No. 33
QVQLQQPGAELVRPGASVKLSCKASGYTFTNYWINWVKQRPGQGLEWIGN

IYPSDSFTNYNQKFKDKATLTVDKSSSTAYMQLSSPTSEDSAVYYCTRDT

QERSWYFDVWGAGTTVTVSSDVVMTQTPLSLPVSLGDQASISCRSSQSLV

HSNGNTYLHWYLQKPGQSPKLLIYKVSNRFSGVPDRFSGSGSGTDFTLKI

SRVEAEDLGLYFCSQSTHVPWTFGGGTKLEIK (Humanised CD22ALAb scFv sequence)
                                        SEQ ID No. 34
EVQLVESGAEVKKPGSSVKVSCKASGYTFTNYWINWVRQAPGQGLEWIGN

IYPSDSFTNYNQKFKDRATLTVDKSTSTAYLELRNLRSDDTAVYYCTRDT

QERSWYFDVWGQGTLVTVSSDIVMTQSPATLSVSPGERATLSCRSSQSLV

HSNGNTYLHWYQQKPGQAPRLLIYKVSNRFSGVPARFSGSGSGVEFTLTI

SSLQSEDFAVYYCSQSTHVPWTFGQGTRLEIK
```

The scFv may be in a VH-VL orientation (as shown in SEQ ID Nos 33 and 34) or a VL-VH orientation.

The CAR of the present invention may comprise one of the following VH sequences:

```
(Murine CD22ALAb VH sequence)
                                        SEQ ID No. 35
QVQLQQPGAELVRPGASVKLSCKASGYTFTNYWINWVKQRPGQGLEWIGN

IYPSDSFTNYNQKFKDKATLTVDKSSSTAYMQLSSPTSEDSAVYYCTRDT

QERSWYFDVWGAGTTVTVSS (Humanised CD22ALAb VH sequence)
                                        SEQ ID No. 36
EVQLVESGAEVKKPGSSVKVSCKASGYTFTNYWINWVRQAPGQGLEWIGN

IYPSDSFTNYNQKFKDRATLTVDKSTSTAYLELRNLRSDDTAVYYCTRDT

QERSWYFDVWGQGTLVTVSS
```

The CAR of the present invention may comprise one of the following VL sequences:

(Murine CD22ALAb VL sequence)
SEQ ID No. 37
DVVMTQTPLSLPVSLGDQASISCRSSQSLVHSNGNTYLHWYLQKPGQSPK

LLIYKVSNRFSGVPDRFSGSGSGTDFTLKISRVEAEDLGLYFCSQSTHVP

WTFGGGTKLEIK (Humanised CD22ALAb VL sequence)
SEQ ID No. 38
DIVMTQSPATLSVSPGERATLSCRSSQSLVHSNGNTYLHWYQQKPGQAPR

LLIYKVSNRFSGVPARFSGSGSGVEFTLTISSLQSEDFAVYYCSQSTHVP

WTFGQGTRLEIK

The CAR of the invention may comprise a variant of the sequence shown as SEQ ID No. 33, 34, 35, 36, 37 or 38 having at least 80, 85, 90, 95, 98 or 99% sequence identity, provided that the variant sequence retain the capacity to bind CD22 (when in conjunction with a complementary VL or VH domain, if appropriate).

B-Cell Antigen Expression During B-Cell Ontogeny and Subsequent Tumours

CD19 is widely considered a pan-B antigen, although very occasionally, it may display some lineage infidelity. The CD19 molecule comprises of two extracellular IgSF domains separated by a smaller domain and a long intracytoplasmic tail, nearly as big as the extracellular portion of the molecule, carrying one ITAM. CD19 is a key molecule in the development and activation of B-cells. CD22 is a molecule of the IgSF which may exist in two isoforms, one with seven domains and an intra-cytoplasmic tail comprising of three ITIMs (immune receptor tyrosine-based inhibitory motifs) and an ITAM; and a splicing variant which instead comprises of five extracellular domains and an intra-cytoplasmic tail carrying one ITIM. CD22 is thought to be an inhibitory receptor involved in the control of B-cell responses to antigen. Like CD19, CD22 is widely considered to be a pan-B antigen, although expression on some non-lymphoid tissue has been described (Wen et al. (2012) J. Immunol. Baltim. Md. 1950 188, 1075-1082). Targeting of CD22 with therapeutic monoclonal antibodies and immunoconjugates has entered clinical testing. Generation of CD22 specific CARs have been described (Haso et al, 2013, Blood: Volume 121; 7: 1165-74, and James et al 2008, Journal of immunology, Volume 180; Issue 10; Pages 7028-38).

Detailed immunophenotyping studies of B-cell leukaemias shows that while surface CD19 is always present, surface CD22 is almost always present. For instance, Raponi et al (2011, as above) studied the surface antigen phenotype of 427 cases of B-ALL and found CD22 present in 341 of cases studied.

The eventuality of CD19 down-regulation after CAR19 targeting described above may be explained by the Goldie-Coldman hypothesis. The Goldie-Coldman hypothesis predicts that tumor cells mutate to a resistant phenotype at a rate dependent on their intrinsic genetic instability and that the probability that a cancer would contain resistant clones depends on the mutation rate and the size of the tumor. While it may be difficult for cancer cells to become intrinsically resistant to the direct killing of cytotoxic T-cells, antigen loss remains possible. Indeed this phenomenon has been reported before with targeting melanoma antigens and EBV-driven lymphomas. According to Goldie-Coldman hypothesis, the best chance of cure would be to simultaneously attack non-cross resistant targets. Given that CD22 is expressed on nearly all cases of B-ALL, simultaneous CAR targeting of CD19 along with CD22 may reduce the emergence of resistant CD19 negative clones.

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain of the CAR which binds to CD19 may be any domain which is capable of binding CD19. For example, the antigen binding domain may comprise a CD19 binder as described in Table 1.

The antigen binding domain of the CAR which binds to CD19 may comprise a sequence derived from one of the CD19 binders shown in Table 2.

TABLE 2

| Binder | References |
| --- | --- |
| HD63 | Pezzutto (Pezzutto, A. et al. J. Immunol. Baltim. Md 1950 138, 2793-2799 (1987) |
| 4g7 | Meeker et al (Meeker, T. C. et al. *Hybridoma* 3, 305-320 (1984) |
| Fmc63 | Nicholson et al (Nicholson, I. C. et al. Mol. Immunol. 34, 1157-1165 (1997) |
| B43 | Bejcek et al (Bejcek, B. E. et al. *Cancer Res.* 55, 2346-2351 (1995) |
| SJ25C1 | Bejcek et al (1995, as above) |
| BLY3 | Bejcek et al (1995, as above) |
| B4, or re-surfaced, or humanized B4 | Roguska et al (Roguska, M. A. et al. Protein Eng. 9, 895-904 (1996) |
| HB12b, optimized and humanized | Kansas et al (Kansas, G. S. & Tedder, T. F. J. Immunol. Baltim. Md 1950 147, 4094-4102 (1991); Yazawa et al (Yazawa et al Proc. Natl. Acad. Sci. U.S.A. 102, 15178-15183 (2005); Herbst et al (Herbst, R. et al. J. Pharmacol. Exp. Ther. 335, 213-222 (2010) |

The antigen binding domain of the CAR which binds to CD22 may be any domain which is capable of binding CD22. For example, the antigen binding domain may comprise a CD22 binder as described in Table 3.

TABLE 3

| Binder | References |
| --- | --- |
| M5/44 or humanized M5/44 | John et al (J. Immunol. Baltim. Md 1950 170, 3534-3543 (2003); and DiJoseph et al (Cancer Immunol. Immunother. CII 54, 11-24 (2005) |
| M6/13 | DiJoseph et al (as above) |
| HD39 | Dorken et al (J. Immunol. Baltim. Md 1950 136, 4470-4479 (1986) |
| HD239 | Dorken et al (as above) |
| HD6 | Pezzutto et al (J. Immunol. Baltim. Md 1950 138, 98-103 (1987) |
| RFB-4, or humanized RFB-4, or affinity matured | Campana et al (J. Immunol. Baltim. Md 1950 134, 1524-1530 (1985); Krauss et al (Protein Eng. 16, 753-759 (2003), Kreitman et al (J. Clin. Oncol. Off. J. Am. Soc. Clin. Oncol. 30, 1822-1828 (2012)) |

TABLE 3-continued

| Binder | References |
| --- | --- |
| To15 | Mason et al (Blood 69, 836-840 (1987)) |
| 4KB128 | Mason et al (as above) |
| S-HCL1 | Schwarting et al (Blood 65, 974-983 (1985)) |
| mLL2 (EPB-2), or humanized mLL2-hLL2 | Shih et al (Int. J. Cancer J. Int. Cancer 56, 538-545 (1994)), Leonard et al (J. Clin. Oncol. Off. J. Am. Soc. Clin. Oncol. 21, 3051-3059 (2003)) |
| M971 | Xiao et al (mAbs 1, 297-303 (2009)) |
| BC-8 | Engel et al (J. Exp. Med. 181, 1581-1586 (1995)) |
| HB22-12 | Engel et al (as above) |

Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In the cell of the present invention, the first and second CARs may comprise different spacer molecules. For example, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

The spacer for the anti-CD19 CAR may comprise a CD8 stalk spacer, or a spacer having a length equivalent to a CD8 stalk spacer. The spacer for the anti-CD19 CAR may have at least 30 amino acids or at least 40 amino acids. It may have between 35-55 amino acids, for example between 40-50 amino acids. It may have about 46 amino acids.

The spacer for the anti-CD22 CAR may comprise an IgG1 hinge spacer, or a spacer having a length equivalent to an IgG1 hinge spacer. The spacer for the anti-CD22 CAR may have fewer than 30 amino acids or fewer than 25 amino acids. It may have between 15-25 amino acids, for example between 18-22 amino acids. It may have about 20 amino acids.

Examples of amino acid sequences for these spacers are given below:

```
(hinge-CH2CH3 of human IgG1)
                                                SEQ ID No. 4
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID No. 5 (human CD8 stalk):
ITTPAPRPPTPAPTIASQPLSLRPEACRPAAGGAVHIRGLDFACDI

SEQ ID No. 6 (human IgG1 hinge):
AEPKSPDKTHTCPPCPKDPK (CD2 ectodomain)
                                                SEQ ID No. 7
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD (CD34 ectodomain)
                                                SEQ ID No. 8
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT
```

Since CARs are typically homodimers (see FIG. 1A), cross-pairing may result in a heterodimeric chimeric antigen receptor. This is undesirable for various reasons, for example: (1) the epitope may not be at the same "level" on the target cell so that a cross-paired CAR may only be able to bind to one antigen; (2) the VH and VL from the two different scFv could swap over and either fail to recognize target or worse recognize an unexpected and unpredicted antigen. The spacer of the first CAR may be sufficiently different from the spacer of the second CAR in order to avoid cross-pairing. The amino acid sequence of the first spacer may share less that 50%, 40%, 30% or 20% identity at the amino acid level with the second spacer.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good receptor stability.

The transmembrane domain may be derived from human Tyrp-1. The tyrp-1 transmembrane sequence is shown as SEQ ID No. 45.

```
                                               SEQ ID No. 45
              IIAIAVVGALLLVALIFGTASYLI
```

Activating Endodomain

The endodomain is the signal-transmission portion of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The cell of the present invention comprises two CARs, each with an endodomain.

The endodomain of the first CAR and the endodomain of the second CAR may comprise:

(i) an ITAM-containing endodomain, such as the endodomain from CD3 zeta; and/or
(ii) a co-stimulatory domain, such as the endodomain from CD28; and/or
(iii) a domain which transmits a survival signal, for example a TNF receptor family endodomain such as OX-40 or 4-1 BB.

In one arrangement the co-stimulatory and survival signal-producing domains are "shared" between the two (or more) CARs in an OR gate. For example, where an OR gate has two CARs, CAR A and CAR B, CAR A may comprise a co-stimulatory domain (e.g. CD28 endodomain) and CAR B may comprise a TNF receptor family endodomain, such as OX-40 or 4-1 BB.

An endodomain which contains an ITAM motif can act as an activation endodomain in this invention. Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I. Typically, but not always, two of these motifs are separated by between 6 and 8 amino acids in the tail of the molecule (YxxL/Ix (6-8)YxxL/1). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000/063372, which relates to synthetic signalling molecules).

The transmembrane and intracellular T-cell signalling domain (endodomain) of a CAR with an activating endodomain may comprise the sequence shown as SEQ ID No. 9, 10 or 11 or a variant thereof having at least 80% sequence identity.

SEQ ID No. 9 comprising CD28 transmembrane domain and CD3 Z endodomain

FWVLVVVGGVLACYSLLVTVAFIIFWVRRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID No. 10 comprising CD28 transmembrane domain and CD28 and CD3 Zeta endodomains

FWVLVVVGGVLACYSLLVTVAFIIFWVRSKRSRLLHSDYMNMTPRRPGPT

RKHYQPYAPPRDFAAYRSRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR

SEQ ID No. 11 comprising CD28 transmembrane domain and CD28, OX40 and CD3 Zeta endodomains.

FWVLVVVGGVLACYSLLVTVAFIIFWVRSKRSRLLHSDYMNMTPRRPGPT

RKHYQPYAPPRDFAAYRSRDQRLPPDAHKPPGGGSFRTPIQEEQADAHST

LAKIRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR

A variant sequence may have at least 80%, 85%, 90%, 95%, 98% or 99% sequence identity to SEQ ID No. 9, 10 or 11, provided that the sequence provides an effective transmembrane domain and an effective intracellular T cell signaling domain.

"Split" or Gate Endodomains

The present invention provides an OR gate in which the co-stimulatory/survival signal domains are "split" between the two CARs.

In this respect, the present invention provides a cell which co-expresses a first chimeric antigen receptor (CAR) and second CAR at the cell surface, each CAR comprising an intracellular signalling domain, wherein the intracellular signalling domain of the first CAR comprises a co-stimulatory domain; and the intracellular signalling domain of the second CAR comprises a TNF receptor family endodomain.

The first and second CARs may bind to different antigens. For example, the first CAR may bind CD19 and the second CAR may bind CD22; alternatively the first CAR may bind CD22 and the second CAR may bind CD19.

The intracellular signalling domain of the first CAR comprises a co-stimulatory domain and does not comprise a domain which transmits survival signals (such as a TNF receptor family endodomain). The intracellular signalling domain of the second CAR comprises a TNF receptor family endodomain and does not comprise a co-stimulatory domain (such as CD28 endodomain).

The co-stimulatory domain may be a CD28 co-stimulatory domain. The CD28 co-stimulatory domain may have the sequence shown as SEQ ID No. 41.

(CD28 co-stimulatory endodomain)
SEQ ID No. 41
SKRSRLLHSDYMNMTPRRPGPTRKHYQPYAPPRDFAAYRS The CAR of the invention may comprise a variant of the sequence shown as SEQ ID No. 41 having at least 80, 85, 90, 95, 98 or 99% sequence identity, provided that the variant sequence retains the capacity to co-stimulate T cells upon antigen recognition, i.e. provide signal 2 to T cells.

The TNF receptor family endodomain may be an OX40 or 4-1 BB endodomain. The OX40 endodomain may have the sequence shown as SEQ ID No. 42. The 4-1BB endodomain may have the sequence shown as SEQ ID No. 43.

(OX40 endodomain)
SEQ ID No. 42
RDQRLPPDAHKPPGGGSFRTPIQEEQADAHSTLAKI (4-1 BB endodomain)
SEQ ID No. 43
KRGRKKLLYIFKQPFMRPVQTTQEEDGCSCRFPEEEEGGCEL The CAR of the invention may comprise a variant of the sequence shown as SEQ ID No. 42 or 43 having at least 80, 85, 90, 95, 98 or 99% sequence identity, provided that the variant sequence retains the capacity to transmit a survival signal to T cells upon antigen recognition.

The intracellular signalling domain of the first and/or the second CAR may also comprise an ITAM-containing domain, such as a CD3 zeta domain. The CD3 zeta domain may have the sequence shown as SEQ ID No. 44.

(CD3zeta endodomain)

SEQ ID No. 44
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

The CAR of the invention may comprise a variant of the sequence shown as SEQ ID No. 44 having at least 80, 85, 90, 95, 98 or 99% sequence identity, provided that the variant sequence retains the capacity to induce T-cell signalling upon antigen recognition, i.e. provide signal 1 to T cells.

The first CAR may have the structure:

AgB1-spacer1-TM1-costim-ITAM in which:
AgB1 is the antigen-binding domain of the first CAR;
spacer 1 is the spacer of the first CAR;
TM1 is the transmembrane domain of the first CAR;
costim is a co-stimulatory domain; and
ITAM is an ITAM-containing endodomain.
"Costim" may be a CD28 co-stimulatory domain.
"ITAM" may be a CD3 zeta endodomain.
The second CAR may have the structure:

AgB2-spacer2-TM2-TNF-ITAM in which:
AgB2 is the antigen-binding domain of the second CAR;
spacer 2 is the spacer of the second CAR;
TM2 is the transmembrane domain of the second CAR;
TNF is a TNF receptor endodomain; and
ITAM is an ITAM-containing endodomain.
"TNF" may be a TNF receptor endodomain such as the OX40 or 4-1 BB endodomains.

There is also provided a nucleic acid sequence encoding both the first and second chimeric antigen receptors (CARs) with "split" endodomains; and a kit comprising two nucleic acids one encoding a first CAR and one encoding a second CAR comprising split endodomains as defined above.

Co-Expression Site

The second aspect of the invention relates to a nucleic acid which encodes the first and second CARs.

The nucleic acid may produce a polypeptide which comprises the two CAR molecules joined by a cleavage site. The cleavage site may be self-cleaving, such that when the polypeptide is produced, it is immediately cleaved into the first and second CARs without the need for any external cleavage activity.

Various self-cleaving sites are known, including the Foot-and-Mouth disease virus (FMDV) 2A peptide and similar sequence (Donnelly et al, Journal of General Virology (2001), 82, 1027-1041), for instance like the 2A-like sequence from Thosea asigna virus which has the sequence shown as SEQ ID No. 12:

SEQ ID No. 12
RAEGRGSLLTCGDVEENPGP.

The co-expressing sequence may be an internal ribosome entry sequence (IRES). The co-expressing sequence may be an internal promoter Cell The present invention relates to a cell which co-expresses a first CAR and a second CAR at the cell surface, wherein one CAR binds CD19 and the other CAR binds CD22.

The cell may be any eukaryotic cell capable of expressing a CAR at the cell surface, such as an immunological cell.

In particular the cell may be an immune effector cell such as a T cell or a natural killer (NK) cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The T cell of the invention may be any of the T cell types mentioned above, in particular a CTL.

Natural killer (NK) cells are a type of cytolytic cell which forms part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

CAR-expressing cells, such as CAR-expressing T or NK cells may either be created ex vivo either from a patient's own peripheral blood (1st party), or in the setting of a haematopoietic stem cell transplant from donor peripheral blood (2nd party), or peripheral blood from an unconnected donor (3rd party).

The present invention also provide a cell composition comprising CAR expressing T cells and/or CAR expressing NK cells according to the present invention. The cell composition may be made by transducing a blood-sample ex vivo with a nucleic acid according to the present invention.

Alternatively, CAR-expressing cells may be derived from ex vivo differentiation of inducible progenitor cells or embryonic progenitor cells to the relevant cell type, such as T cells. Alternatively, an immortalized cell line such as a T-cell line which retains its lytic function and could act as a therapeutic may be used.

In all these embodiments, CAR cells are generated by introducing DNA or RNA coding for the CARs by one of many means including transduction with a viral vector, transfection with DNA or RNA.

A CAR T cell of the invention may be an ex vivo T cell from a subject. The T cell may be from a peripheral blood mononuclear cell (PBMC) sample. T cells may be activated and/or expanded prior to being transduced with CAR-encoding nucleic acid, for example by treatment with an anti-CD3 monoclonal antibody.

A CAR T cell of the invention may be made by:
(i) isolation of a T cell-containing sample from a subject or other sources listed above; and
(ii) transduction or transfection of the T cells with one or more nucleic acid sequence(s) encoding the first and second CAR.

The T cells may then by purified, for example, selected on the basis of co-expression of the first and second CAR.

Nucleic Acid Sequences

The second aspect of the invention relates to one or more nucleic acid sequence(s) which codes for a first CAR and a second CAR as defined in the first aspect of the invention.

The nucleic acid sequence may be, for example, an RNA, a DNA or a cDNA sequence.

The nucleic acid sequence may encode one chimeric antigen receptor (CAR) which binds to CD19 and another CAR which binds to CD22.

The nucleic acid sequence may have the following structure:

AgB1-spacer1-TM1-coexpr-AbB2-spacer2-TM2 in which

AgB1 is a nucleic acid sequence encoding the antigen-binding domain of a first CAR; spacer 1 is a nucleic acid sequence encoding the spacer of a first CAR;

TM1 is a nucleic acid sequence encoding the transmembrane domain of a first CAR; coexpr is a nucleic acid sequence enabling co-expression of both CARs AgB2 is a nucleic acid sequence encoding the antigen-binding domain of a second CAR; spacer 2 is a nucleic acid sequence encoding the spacer of a second CAR;

TM2 is a nucleic acid sequence encoding the transmembrane domain of a second CAR; which nucleic acid sequence, when expressed in a T cell, encodes a polypeptide which is cleaved at the cleavage site such that the first and second CARs are co-expressed at the cell surface.

The first CAR may bind CD19 and the second CAR may bind CD22. Alternatively the first CAR may bind CD22 and the second CAR may bind CD19.

Alternative codons may be used in regions of sequence encoding the same or similar amino acid sequences, in order to avoid homologous recombination.

Due to the degeneracy of the genetic code, it is possible to use alternative codons which encode the same amino acid sequence. For example, the codons "ccg" and "cca" both encode the amino acid proline, so using "ccg" may be exchanged for "cca" without affecting the amino acid in this position in the sequence of the translated protein.

The alternative RNA codons which may be used to encode each amino acid are summarised in Table 3.

TABLE 3

|   | U | C | A | G |
|---|---|---|---|---|
| U | UUU UUC } Phe (F)<br>UUA UUG } Leu (L) | UCU UCC UCA UCG } Ser (S) | UAU UAC } Tyr (Y)<br>UAA Ocher<br>UAG Amber | UGU UGC } Cys (C)<br>UGA Opal<br>UGG Trp(W) |
| C | CUU CUC CUA CUG } Leu (L) | CCU CCC CCA CCG } Pro (P) | CAU CAC } His (H)<br>CAA CAG } Gln (Q) | CGU CGC CGA CGG } Arg (R) |
| A | AUU AUC AUA } Ile (LI)<br>AUG Met(M) | ACU ACC ACG ACG } Thr (T) | AAU AAC } Asn (N)<br>AAA AAG } Lys (K) | AGU AGC } Ser (S)<br>AGA AGG } Arg (R) |

TABLE 3-continued

| | U | C | A | G |
|---|---|---|---|---|
| G | GUU ⎫<br>GUC ⎬ Val<br>GUA ⎥ (V)<br>GUG ⎭ | GCU ⎫<br>GCC ⎬ Ala<br>GCA ⎥ (A)<br>GCG ⎭ | GAU ⎱ Asp<br>GAU ⎰ (D)<br>GAA ⎱ Glu<br>GAG ⎰ (E) | GGU ⎫<br>GGC ⎬ Gly<br>GGA ⎥ (G)<br>GGG ⎭ |

Figure 4:
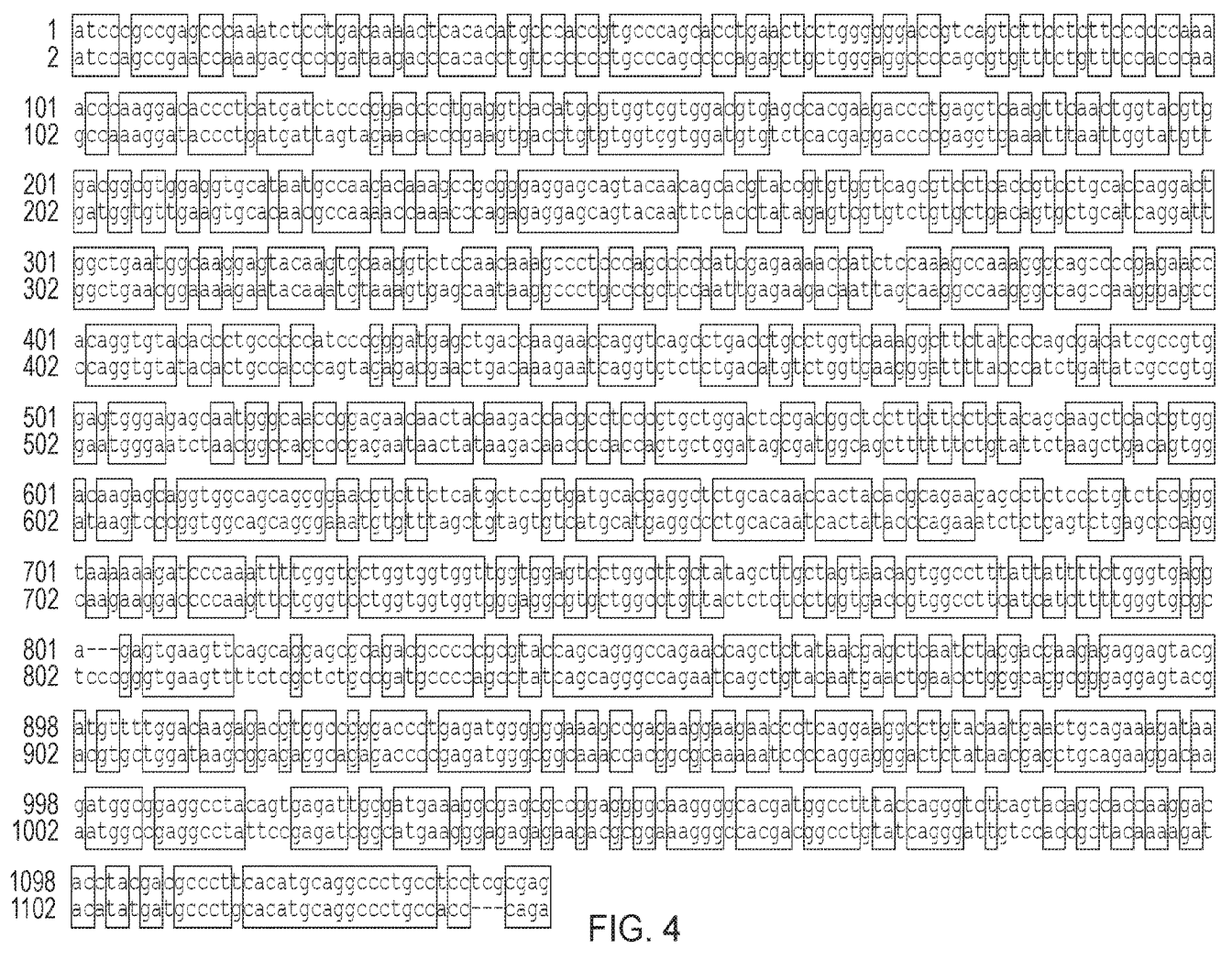

Alternative codons may be used in the portions of nucleic acid sequence which encode the spacer of the first CAR and the spacer of the second CAR, especially if the same or similar spacers are used in the first and second CARs. FIG. 4 shows two sequences encoding the spacer HCH2CH3—hinge, in one of which alternative codons have been used.

Alternative codons may be used in the portions of nucleic acid sequence which encode the transmembrane domain of the first CAR and the transmembrane of the second CAR, especially if the same or similar transmembrane domains are used in the first and second CARs. FIG. 4 shows two sequences encoding the CD28 transmembrane domain, in one of which alternative codons have been used.

Alternative codons may be used in the portions of nucleic acid sequence which encode all or part of the endodomain of the first CAR and all or part of the endodomain of the second CAR. Alternative codons may be used in the CD3 zeta endodomain. FIG. 4 shows two sequences encoding the CD3 zeta endodomain, in one of which alternative codons have been used.

Alternative codons may be used in one or more co-stimulatory domains, such as the CD28 endodomain.

Alternative codons may be used in one or more domains which transmit survival signals, such as OX40 and 41BB endodomains.

Alternative codons may be used in the portions of nucleic acid sequence encoding a CD3zeta endodomain and/or the portions of nucleic acid sequence encoding one or more costimulatory domain(s) and/or the portions of nucleic acid sequence encoding one or more domain(s) which transmit survival signals.

Vector

The present invention also provides a vector, or kit of vectors which comprises one or more CAR-encoding nucleic acid sequence(s). Such a vector may be used to introduce the nucleic acid sequence(s) into a host cell so that it expresses the first and second CARs.

The vector may, for example, be a plasmid or a viral vector, such as a retroviral vector or a lentiviral vector, or a transposon based vector or synthetic mRNA.

The vector may be capable of transfecting or transducing a T cell.

Pharmaceutical Composition

The present invention also relates to a pharmaceutical composition containing a plurality of CAR-expressing cells, such as T cells or NK cells according to the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention are capable of killing cancer cells, such as B-cell lymphoma cells. CAR-expressing cells, such as T cells, may either be created ex vivo either from a patient's own peripheral blood (1st party), or in the setting of a haematopoietic stem cell transplant from donor peripheral blood (2nd party), or peripheral blood from an unconnected donor (3rd party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

The cells of the present invention may be capable of killing target cells, such as cancer cells. The target cell is recognisable by expression of CD19 or CD22.

TABLE 4 expression of lymphoid antigens on lymphoid leukaemias

| | CD19 | CD22 | CD10 | CD7 | CD5 | CD3 | clg μ | slg μ |
|---|---|---|---|---|---|---|---|---|
| Early pre-B | 100 | >95 | 95 | 5 | 0 | 0 | 0 | 0 |
| Pre-B | 100 | 100 | >95 | 0 | 0 | 0 | 100 | 0 |
| Transitional pre-B | 100 | 100 | 50 | 0 | 0 | 0 | 100 | 0 |
| B | 100 | 100 | 50 | 0 | 0 | 0 | >95 | >95 |
| T | <5 | 0 | 0 | 100 | 95 | 100 | 0 | 0 |

Taken from Campana et al. (Immunophenotyping of leukemia. J. Immunol. Methods 243, 59-75 (2000)). clg μ—cytoplasic Immunoglobulin heavy chain; slg μ—surface Immunoglobulin heavy chain.

Figure 2:
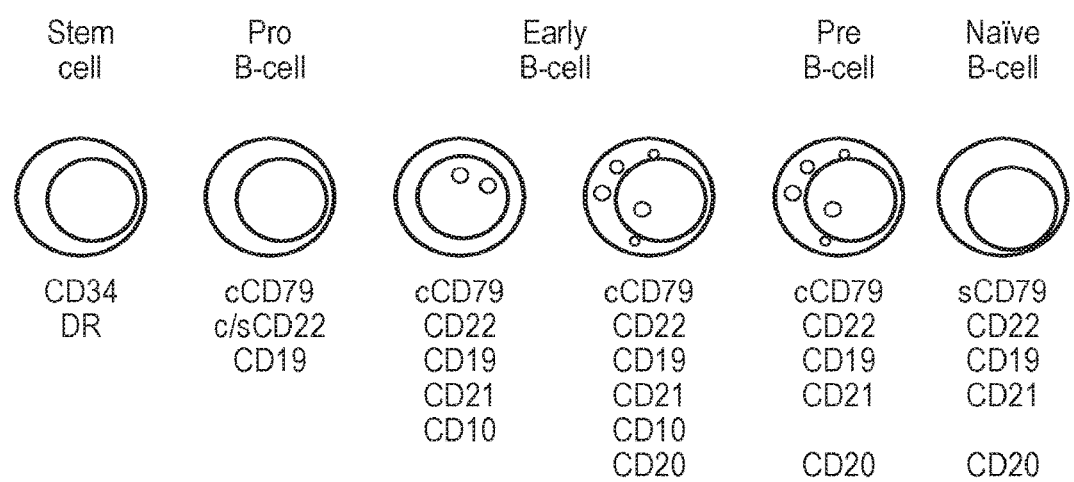
FIG. 2: B-cell maturation pathway/B-cell ontogeny. DR=HLA-DR; cCD79=cytoplasmic CD79; cCD22=cytoplasmic CD22. Both CD19 and CD22 antigens are expressed during early stages in B-cell maturation. It is these cells that develop into B-cell acute leukaemias. Targeting both CD19 as well as CD22 simultaneously is most suited for targeting B-cell acute leukaemias.
Figure 3A:
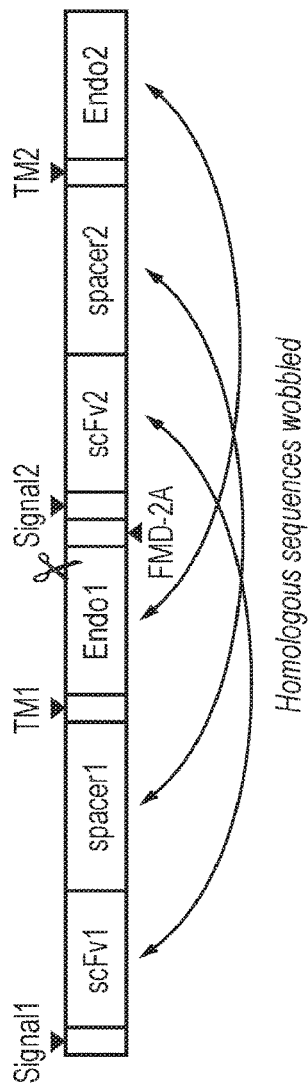
FIGS. 3A-3B: Strategies for design of an anti-CD19 OR CD22 CAR cassette. Binders which recognize CD19 and binders which recognize CD22 are selected. An optimal spacer domain and signalling domain is selected for each CAR.
Figure 3B:
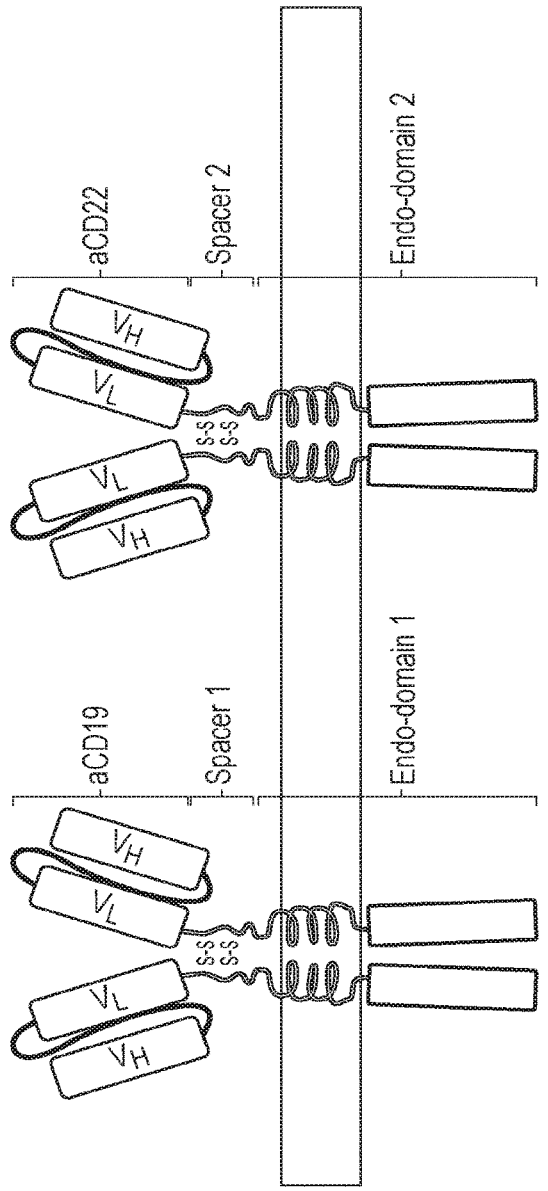

The expression of commonly studied lymphoid antigens on different types of B-cell leukaemias closely mirrors that of B-cell ontogeny (see FIG. 2).

The T cells of the present invention may be used to treat cancer, in particular B-cell malignancies.

Examples of cancers which express CD19 or CD22 are B-cell lymphomas, including Hodgkin's lymphoma and non-Hodgkins lymphoma; and B-cell leukaemias.

For example the B-cell lymphoma may be Diffuse large B cell lymphoma (DLBCL), Follicular lymphoma, Marginal zone lymphoma (MZL) or Mucosa-Associated Lymphatic Tissue lymphoma (MALT), Small cell lymphocytic lymphoma (overlaps with Chronic lymphocytic leukemia), Mantle cell lymphoma (MCL), Burkitt lymphoma, Primary mediastinal (thymic) large B-cell lymphoma, Lymphoplasmacytic lymphoma (may manifest as Waldenström macroglobulinemia), Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma or Primary central nervous system lymphoma.

The B-cell leukaemia may be acute lymphoblastic leukaemia, B-cell chronic lymphocytic leukaemia, B-cell pro-lymphocytic leukaemia, precursor B lymphoblastic leukaemia or hairy cell leukaemia.

The B-cell leukaemia may be acute lymphoblastic leukaemia.

Treatment with the T cells of the invention may help prevent the escape or release of tumour cells which often occurs with standard approaches.

The invention will now be further described by way of Examples, which are meant to serve to assist one of ordinary skill in the art in carrying out the invention and are not intended in any way to limit the scope of the invention.

EXAMPLES

Example 1—Proof-of-Concept of a CD19/CD22 Logical 'OR' Gate

A CD19 'OR' CD22 CAR gate was constructed by co-expression of a CD19 and a CD22 CAR in the same vector. The anti-CD19 binder was a scFv derived from the re-surfaced B4 antibody (Roguska et al. (1996) Protein Eng. 9, 895-904), and the anti-CD22 binder was a scFv derived from the humanized RFB4 antibody. A human IgG1 hinge-CH2-CH3 spacer was used for both CARs, the coding sequence of which was codon-wobbled to avoid homologous recombination by the integrating vector. The TM domain in both CARs was derived from that of CD28, and both CAR endodomains comprised of CD3-Zeta. Once again, these homologous sequences were codon-wobbled. Co-expression was achieved by cloning the two CARs in frame separated by a FMD-2A peptide. The nucleic acid and amino acid sequence of the CD19/CD22 'OR' gate construct are shown as SEQ ID NOs: 13 and 14; respectively.

```
                                               SEQ ID NO: 13
ATGAGCCTGCCCGTGACCGCCCTGCTGCTGCCCCTGGCCCTGCTGCTGCA

CGCCGCCAGACCATACCCCTACGACGTGCCCGACTACGCCAGCCTGAGCG

GAGGCGGCGGCAGCCAGGTGCAGCTGGTGCAGAGCGGAGCCGAGGTGAAG

AAGCCTGGCGCCAGCGTGAAGGTGTCCTGTAAGGCCAGCGGCTACACCTT

CACCAGCAACTGGATGCACTGGGTGAGGCAGGCCCCTGGACAGGGACTGG

AGTGGATGGGCGAGATCGACCCCAGCGACAGCTACACCAACTACAACCAG

AAGTTCAAGGGCCGGGTGACCATCACCGTGGATAAGAGCGCCAGCACCGC

CTACATGGAGCTGTCCAGCCTGAGAAGCGAGGATACCGCCGTGTACTACT

GTGCCAGAGGCAGCAACCCCTACTACTACGCTATGGACTACTGGGGCCAG

GGCACCCTGGTGACCGTGTCCAGCGGCGGAGGAGGAAGCGGAGGGGGCGG

ATCTGGCGGCGGAGGGAGCGAGATCGTGCTGACCCAGAGCCCCGCCACCC

TGAGCCTGAGCCCTGGCGAGAGAGCCACCCTGTCCTGTAGCGCCAGCAGC

GGCGTGAATTACATGCACTGGTATCAGCAGAAGCCCGGCCAGGCCCCCAG

AAGATGGATCTACGACACCAGCAAGCTGGCCAGCGGCGTGCCCGCCAGAT

TCAGCGGCAGCGGCTCCGGCACCAGCTACAGCCTGACCATCAGCAGCCTG

GAGCCTGAGGATTTCGCCGTGTATTATTGCCACCAGAGGGGCAGCTACAC

CTTTGGCGGCGGAACAAAGCTGGAGATCAAGCGCTCAGATCCCACCACGA

CGCCAGCGCCGCGACCACCAACACCGGCGCCCACCATCGCGTCGCAGCCC

CTGTCCCTGCGCCCAGAGGCGTGCCGGCCAGCGGCGGGGGCGCAGTGCA

CACGAGGGGCTGGACTTCGCCTGTGATATCTTTTGGGTGCTGGTGGTGG
```

```
                                                 -continued
TTGGTGGAGTCCTGGCTTGCTATAGCTTGCTAGTAACAGTGGCCTTTATT

ATTTTCTGGGTGAGGAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCTCCTCG

CAGAGCCGAGGGCAGGGGAAGTCTTCTAACATGCGGGGACGTGGAGGAAA

ATCCCGGGCCCATGGAGTTTGGGCTGAGCTGGCTTTTTCTTGTGGCTATT

TTAAAAGGTGTCCAGTGCGAGGTGCAGCTGGTGGAGTCTGGGGGAGGCTT

GGTCCAGCCAGGGGGGTCCCTGCGCCTCTCCTGTGCAGCCTCTGGATTCG

CTTTCAGTATCTATGACATGTCTTGGGTCCGCCAGGTTCCGGGGAAGGGG

CTGGAGTGGGTCTCATATATTAGTAGTGGTGGTGGTACCACCTATTACCC

GGACACTGTGAAGGGCCGCTTCACCATCTCCCGTGACAATTCCCGCAACA

CTCTGGATCTTCAAATGAACAGTCTGCGCGTCGAGGACACGGCTGTCTAT

TATTGTGCGCGTCATAGTGGCTACGGTAGTAGCTACGGGGTTTTGTTTGC

TTACTGGGGCCAAGGAACCCTGGTCACCGTCTCCTCAGGTGGAGGCGGTT

CAGGCGGAGGTGGCTCTGGCGGTGGCGGATCGGACATCCAGATGACTCAG

TCTCCGTCCTCCCTGTCTGCATCTGTAGGAGACCGCGTCACCATCACCTG

CCGTGCAAGTCAGGACATTAGCAATTATTTAAACTGGCTTCAACAGAAAC

CGGGGAAAGCCCCGAAGCTCCTGATTTACTACACATCAATCTTACACTCA

GGAGTCCCGTCACGCTTCAGCGGCAGTGGATCTGGGACAGAATTCACTCT

CACAATCAGCAGCCTGCAGCCGGAAGATTTTGCAACTTATTACTGTCAAC

AGGGTAATACGCTTCCGTGGACGTTTGGCCAGGGGACCAAACTGGAAATC

AAACGTTCGGATCCAGCCGAACCAAAGAGCCCCGATAAGACCCACACCTG

TCCCCCCTGCCCAGCCCCAGAGCTGCTGGGAGGCCCCAGCGTGTTTCTGT

TTCCACCCAAGCCAAAGGATACCCTGATGATTAGTAGAACACCCGAAGTG

ACCTGTGTGGTGGTGGATGTGTCTCACGAGGACCCCGAGGTGAAATTTAA

TTGGTATGTTGATGGTGTTGAAGTGCACAACGCCAAAACCAAACCCAGAG

AGGAGCAGTACAATTCTACCTATAGAGTCGTGTCTGTGCTGACAGTGCTG

CATCAGGATTGGCTGAACGGAAAAGAATACAAATGTAAAGTGAGCAATAA

GGCCCTGCCCGCTCCAATTGAGAAGACAATTAGCAAGGCCAAGGGCCAGC

CAAGGGAGCCCCAGGTGTATACACTGCCACCCAGTAGAGACGAACTGACA

AAGAATCAGGTGTCTCTGACATGTCTGGTGAAGGGATTTTACCCATCTGA

TATCGCCGTGGAATGGGAATCTAACGGCCAGCCCGAGAATAACTATAAGA

CAACCCCACCAGTGCTGGATAGCGATGGCAGCTTTTTTCTGTATTCTAAG

CTGACAGTGGATAAGTCCCGGTGGCAGCAGGGAAATGTGTTTAGCTGTAG

TGTCATGCATGAGGCCCTGCACAATCACTATACCCAGAAATCTCTGAGTC

TGAGCCCAGGCAAGAAGGACCCCAAGTTCTGGGTCCTGGTGGTGGTGGGA

GGCGTGCTGGCCTGTTACTCTCTCCTGGTGACCGTGGCCTTCATCATCTT
```

-continued
TTGGGTGCGCTCCCGGGTGAAGTTTTCTCGCTCTGCCGATGCCCCAGCCT

ATCAGCAGGGCCAGAATCAGCTGTACAATGAACTGAACCTGGGCAGGCGG

GAGGAGTACGACGTGCTGGATAAGCGGAGAGGCAGAGACCCCGAGATGGG

CGGCAAACCACGGCGCAAAAATCCCCAGGAGGGACTCTATAACGAGCTGC

AGAAGGACAAAATGGCCGAGGCCTATTCCGAGATCGGCATGAAGGGAGAG

AGAAGACGCGGAAAGGGCCACGACGGCCTGTATCAGGGATTGTCCACCGC

TACAAAAGATACATATGATGCCCTGCACATGCAGGCCCTGCCACCCAGAT

GA

SEQ ID NO: 14
MSLPVTALLLPLALLLHAARPYPYDVPDYASLSGGGGSQVQLVQSGAEVK

KPGASVKVSCKASGYTFTSNWMHWVRQAPGQGLEWMGEIDPSDSYTNYNQ

KFKGRVTITVDKSASTAYMELSSLRSEDTAVYYCARGSNPYYYAMDYWGQ

GTLVTVSSGGGGSGGGGSGGGGSEIVLTQSPATLSLSPGERATLSCSASS

GVNYMHWYQQKPGQAPRRWIYDTSKLASGVPARFSGSGSGTSYSLTISSL

EPEDFAVYYCHQRGSYTFGGGTKLEIKRSDPTTTPAPRPPTPAPTIASQP

LSLRPEACRPAAGGAVHTRGLDFACDIFWVLVVVGGVLACYSLLVTVAFI

IFWVRRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPRRAEGRGSLLTCGDVEENPGPMEFGLSWLFLVAI

LKGVQCEVQLVESGGGLVQPGGSLRLSCAASGFAFSIYDMSWVRQVPGKG

LEWVSYISSGGGTTYYPDTVKGRFTISRDNSRNTLDLQMNSLRVEDTAVY

YCARHSGYGSSYGVLFAYWGQGTLVTVSSGGGGSGGGGSGGGGSDIQMTQ

SPSSLSASVGDRVTITCRASQDISNYLNWLQQKPGKAPKLLIYYTSILHS

GVPSRFSGSGSGTEFTLTISSLQPEDFATYYCQQGNTLPWTFGQGTKLEI

KRSDPAEPKSPDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGKKDPKFWVLVVVG

GVLACYSLLVTVAFIIFWVRSRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR

To demonstrate co-expression of both CARs, the scFv of each CAR was tagged with an epitope tag (HA or V5 respectively). This subsequent single open-reading frame was cloned into the SFG retroviral vector. T-cells were transduced with this vector and both CARs could be detected on the T-cells surface expressing the cassette by staining with anti-HA and anti-V5 and studying expression by flow cytometry.

Next, T-cells expressing the CD19 OR CD22 CAR gate were challenged with target cells, expressing neither, both or one antigen along with control T-cells which expressed no CARs, or just anti-CD19 CAR alone, or anti-CD22 CAR alone. We found that the OR-gated CAR T-cells could kill target cells expressing either one or both target antigens (FIGS. 5A-5C).

Example 2—Identification and Characterisation of CD19ALAb and CD22ALAb

A CD19-binder (CD19ALAb) was identified, humanised and the binding affinities of both murine and humanised IgGs and scFvs were identified and compared with the "gold-standard" anti-CD19 binder, fmc63. In parallel, and a CD22-binder (CD22ALAb) was identified, humanised and the binding affinities of both murine and humanised IgGs and scFvs were identified and compared with the "gold-standard" anti-CD22 binder, M971.

Experiments were performed on a Biacore T200 instrument using HBS-P as running and dilution buffer. BIAevaluation software Version 2.0 was used for data processing. For binding kinetics, mouse anti-human IgG or goat anti-mouse IgG was covalently coupled to a CM5 Sensor Chip. IgG or scFv-Fc proteins were captured, and various concentrations of interaction partner protein injected over the flow cell at a flow rate of 30 µl/min. Kinetic rate constants were obtained by curve fitting according to a 1:1 Langmuir binding model. Bulk refractive index differences were subtracted using a blank control flow cell in which capture antibody had been immobilized to the same level as the active surface. A double reference subtraction was performed using buffer alone.

Figure 6:
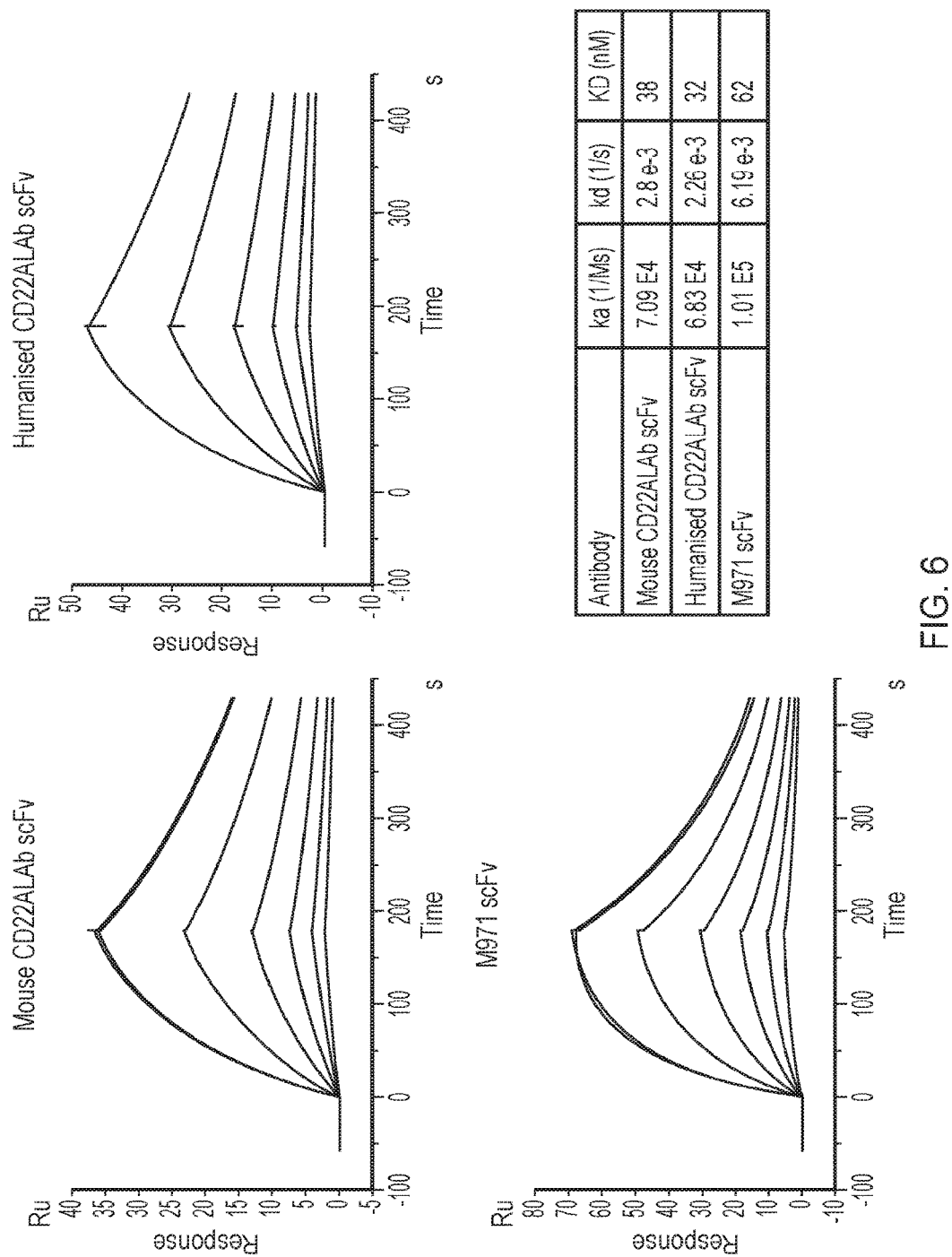
FIG. 6: Biacore affinity determination for murine CD22ALAb scFv, humanised CD22ALAb scFv and M971 scFv
Figure 7:
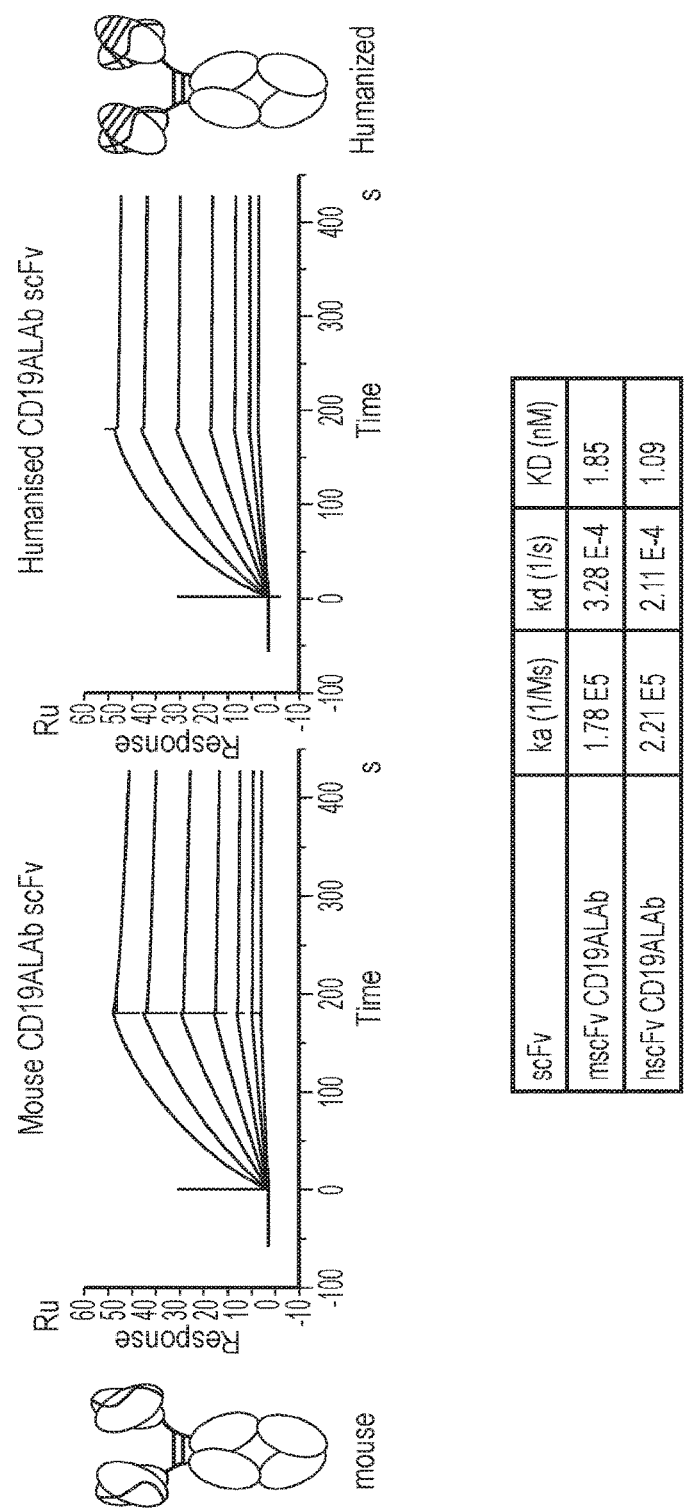
FIG. 7: Biacore affinity determination for murine CD19ALAb scFv and humanised CD19ALAb

The results are shown in FIGS. 6 to 8.

The data show that humanised CD22ALAb has comparable binding affinity to CD22 to murine CD22ALAb (FIG. 6) and similar binding kinetics. Both murine and humanised CD22ALAb in an scFv format have significantly higher binding affinity to CD22 than the gold-standard CD22-binding antibody, M971 (FIG. 6).

Although the binding affinity of murine and humanised CD19ALAb in an IgG format was found to be similar (data not shown), surprisingly the binding affinity of humanised CD19ALAb was found to be higher than murine CD19ALAb in an scFv format (FIG. 7). The binding affinity of CD19ALAb is comparable (possibly slightly better) than that of the gold-standard anti-CD19 Ab, fmc63 (FIG. 8).

Example 3—Comparative Functional Assays with CD19ALAb/Fmc63 CARs and CD22ALAb/M971 CARs The antigen binding domain of a CAR can affect its function. In this study, CARs were created comprising CD19ALAb and CD22ALAb and function was compared with an equivalent CAR having an antigen-binding domain based on fmc63 or M971.

CARs comprising scFvs based on fmc63 (anti-CD19) and M971 (anti-CD22) can be considered as the gold standard antibodies as both CARs are in clinical development.

Figure 9:
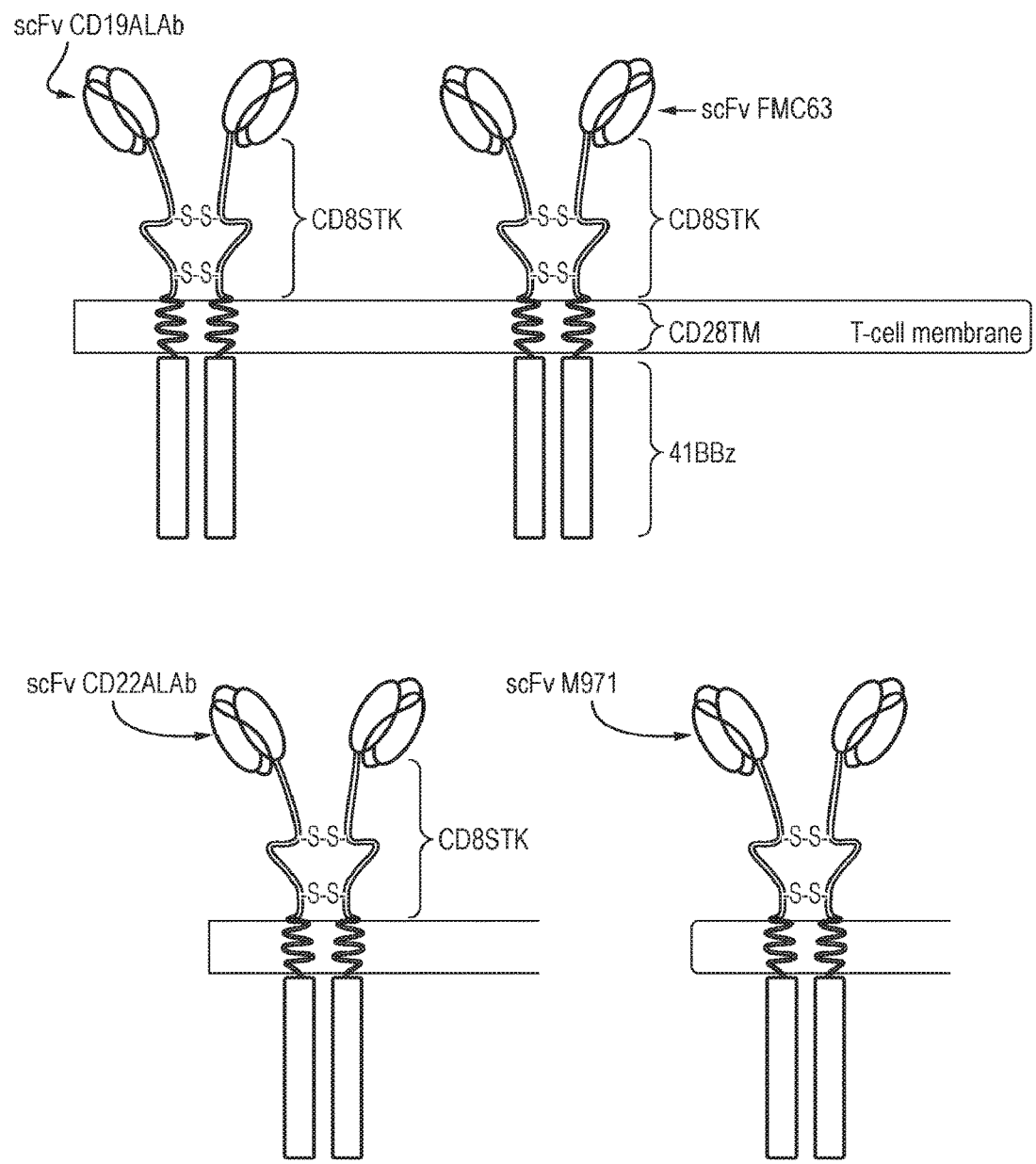
FIG. 9: Schematic diagram illustrating CD19ALAb CAR, fmc63 CAR, CD22ALAb CAR and M971 CAR used in the comparative studies

CARs were constructed and expressed based on CD19ALAb, fmc63, CD22ALAb and M971. Their structure is shown in FIG. 9. The CARs differed solely in their antigen binding domain. In all constructs, the binding domains were linked to the membrane with a CD8 stalk spacer and contained intracellular activatory motifs from 41BB and CD3-zeta.

Retroviruses were produced by transient transfection of 293T cells with plasmids encoding the CARs, gag/pol and the envelope protein RD114. After 3 days the supernatants were harvested and used to transduce PHA/IL2-activated PBMCs with equal titres of retrovirus on retronectin-coated plates. Six days post-transduction CAR-expression was confirmed by flow cytometry and PBMCs were co-cultured in a 1:1 ratio with either CD19+ BFP SupT1 cells (fmc63 and CD19ALAb CARs) or CD22+ BFP SupT1 cells (M971 and CD22ALAb CARs). Target cell killing was assayed after one and three days. Also after one and three days, supernatants were removed and interferon-γ levels were assayed by ELISA.

Figure 10:
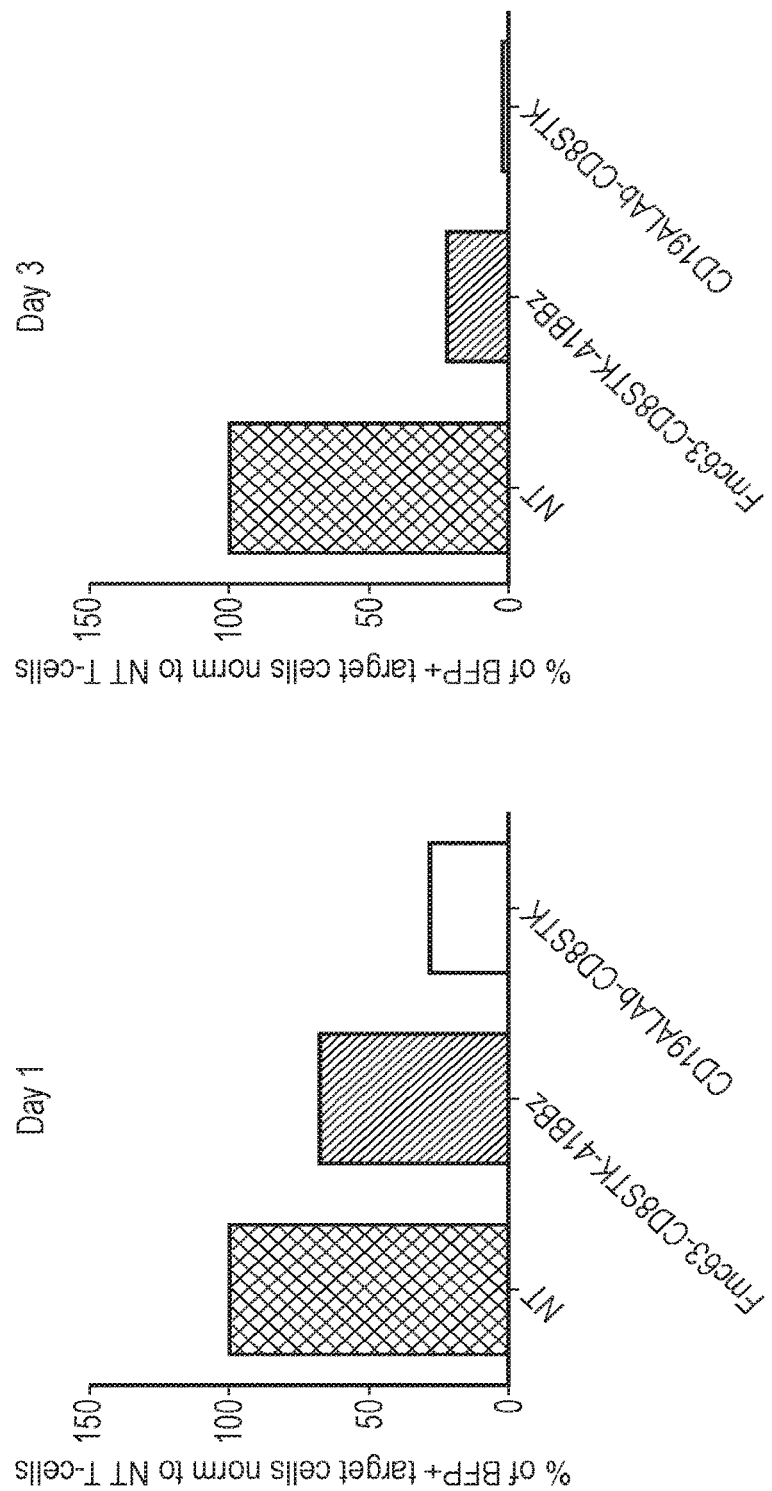
FIG. 10: Killing assay of CD19 positive target cells comparing a CAR with a CD19ALAb antigen binding domain and an equivalent CAR with an fmc63 binding domain.
Figure 11B:
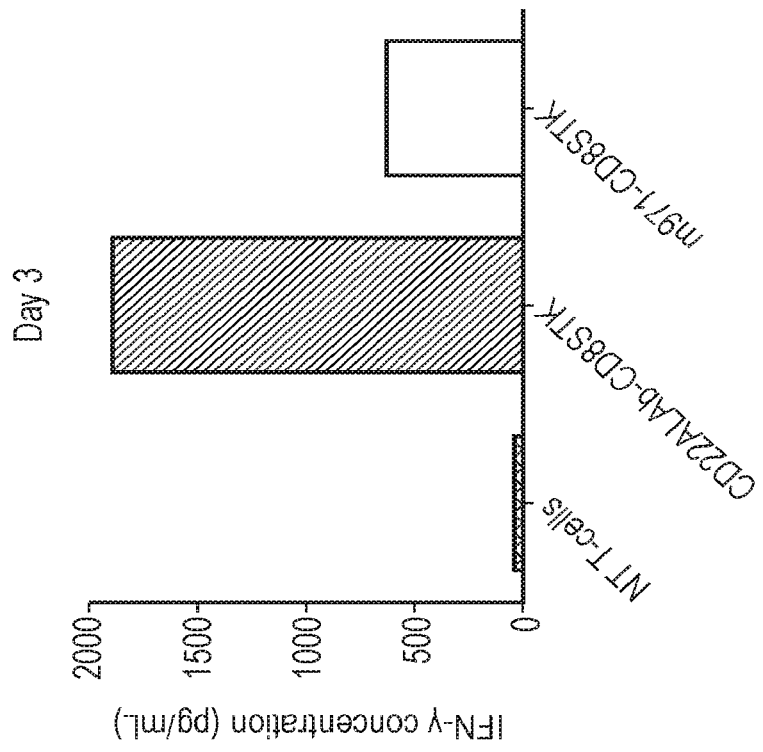
FIGS. 11A-11B.
Figure 11A:
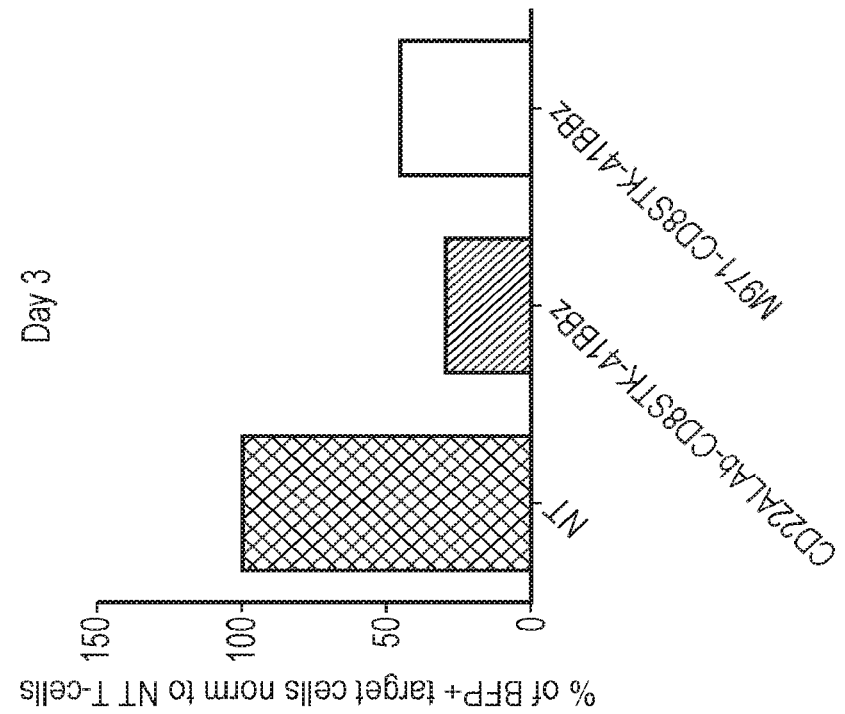

The results are shown in FIGS. 10 and 11A-11B.

As shown in FIG. 10, the CAR with a CD19ALAb antigen binding domain gave more killing of CD19+ve target cells (FIG. 10) at both Day1 and Day 3, than the equivalent CAR with a fmc63 binding domain.

With regard to CD22, the CAR with a CD22ALAb antigen binding domain gave more killing of CD22+ve target cells (FIG. 11A) after three days than the equivalent CAR with an M971 binding domain. IFNγ release was significantly higher with the CD22ALAb CAR than the M971 CAR after the same time frame.

CARs having an antigen-binding domain based on CD19ALAb and CD22ALAb therefore have improved properties in terms of target cell killing than equivalent CARs based on fmc63 and M971.

The CD22ALAb result is particularly surprising, given the findings reported in Haso et al (2013) as above. In that study, different anti-CD22 CARs were made and tested, with binding domains based on the anti-CD22 antibodies HA22, BL22 and m971. HA22 and BL22 scFvs bind to Ig domain 3 of CD22, whereas m971 binds within Ig domain 5-7 of CD22 (see Haso et al (2013) FIG. 2B). It was reported that the m971-derived CAR showed superior target cell killing activity than HA22-derived CAR, which finding is attributed to the importance of the CD22 epitope targeted by the CAR (Haso et al (2013) page 1168, last full paragraph). It is concluded that targeting a membrane proximal domain of CD22 is "the key element" in developing a highly active anti-CD22 CAR (Discussion, last paragraph). Contrary to this finding, the data shown here in FIGS. 11A-11B demonstrate that CD22ALAb, which targets an epitope in Ig domain 3 of CD22—a "membrane distal" epitope compared to the Ig domain 5-7 epitope targeted by m971—has superior target cell killing ability than an m971-based anti-CD22 CAR.

Example 4—Investigating OR Gate Constructs with Different Endodomain Combinations Four OR gate constructs were developed as shown in FIGS. 13A-13D. They all encoded CD19/CD22 OR gates having identical antigen-binding domains, spacer domains and transmembrane domains: the only difference between the construct was in the endodomains, which were as shown in the following Table:

| Construct | CD19 CAR endodomain | CD22 CAR endodomain |
| --- | --- | --- |
| A | 41BB-CD3ζ | 41BB-CD3ζ |
| B | OX40-CD3ζ | OX40-CD3ζ |
| C | 41BB-CD3ζ | CD28-CD3ζ |
| D | OX40-CD3ζ | CD28-CD3ζ |

The capacity of cells expressing each CD19/CD22 OR gate to kill Raji cells in vitro was assayed as described above. Transduced PBMCs expressing the various OR gate combinations were co-cultured for 72 hours with CD19+/CD22+ Raji target cells at both a 1:1 and 1:10 effector:target cell ratio.

Figure 14:
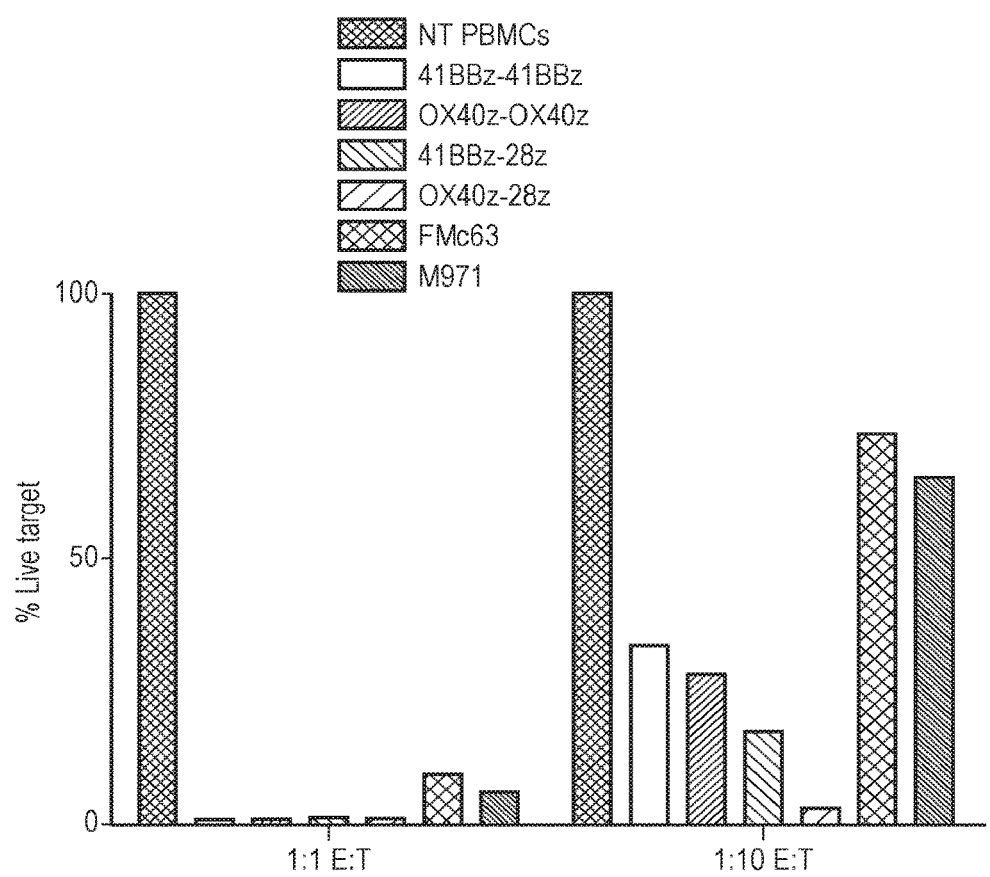
FIG. 14: Target cell killing by cells expressing the constructs shown in FIGS. 13A-13D.

The results are shown in FIG. 14. All four OR gates were found to kill target cells significantly better than the fmc63 and M971 CARs. With the 1:10 effector:target cell ratio, it was shown that the "split" endodomain OR gates, which have 4-1 BBzeta/OX40zeta on one CAR and CD28zeta on the other CAR, had the best killing activity.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A method for treating a cancerous disease, which comprises the step of administering a pharmaceutical composition which comprises a plurality of T cells or natural killer cells to a subject, wherein the T cells or natural killer cells express a chimeric antigen receptor (CAR) comprising a CD22-binding domain which comprises:

a) a heavy chain variable region (VH) having complementarity determining regions (CDRs) with the following sequences:

CDR1
(SEQ ID NO: 27)
NYWIN,

CDR2
(SEQ ID NO: 28)
NIYPSDSFTNYNQKFKD,
and

CDR3
(SEQ ID NO: 29)
DTQERSWYFDV;
and b) a light chain variable region (VL) having CDRs with the following sequences:

CDR1
(SEQ ID NO: 30)
RSSQSLVHSNGNTYLH,

CDR2
(SEQ ID NO: 31)
KVSNRFS,
and

CDR3
(SEQ ID NO: 32)
SQSTHVPWT, wherein cancer cells of the cancerous disease express CD22.

2. A method according to claim 1, wherein the CD22 binding domain comprises a VH domain having the sequence shown as SEQ ID NO: 35 or SEQ ID NO: 36, or a VL domain having the sequence shown as SEQ ID NO: 37 or SEQ ID NO: 38.

3. A method according to claim 1, wherein the CD22 binding domain comprises the sequence shown as SEQ ID NO: 33 or SEQ ID NO: 34.

4. A method according to claim 1, wherein the cancer is a B-cell malignancy.

* * * * *

SEQUENCE LISTING

```
<160> NUMBER OF SEQ ID NOS: 49

<210> SEQ ID NO 1
<211> LENGTH: 21
<212> TYPE: PRT
<213> ORGANISM: Artificial Sequence
<220> FEATURE:
<223> OTHER INFORMATION: Signal peptide

<400> SEQUENCE: 1

Met Gly Thr Ser Leu Leu Cys Trp Met Ala Leu Cys Leu Leu Gly Ala
1               5                   10                  15

Asp His Ala Asp Gly
            20

<210> SEQ ID NO 2
<211> LENGTH: 21
<212> TYPE: PRT
<213> ORGANISM: Artificial Sequence
<220> FEATURE:
<223> OTHER INFORMATION: Signal peptide
```

```
<400> SEQUENCE: 2

Met Ser Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 20
<212> TYPE: PRT
<213> ORGANISM: Artificial Sequence
<220> FEATURE:
<223> OTHER INFORMATION: Signal peptide

<400> SEQUENCE: 3

Met Ala Val Pro Thr Gln Val Leu Gly Leu Leu Leu Leu Trp Leu Thr
1               5                   10                  15

Asp Ala Arg Cys
            20

<210> SEQ ID NO 4
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 4

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230
```

```
<210> SEQ ID NO 5
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 5

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 6
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 6

Ala Glu Pro Lys Ser Pro Asp Lys Thr His Thr Cys Pro Pro Cys Pro
1               5                   10                  15

Lys Asp Pro Lys
            20

<210> SEQ ID NO 7
<211> LENGTH: 185
<212> TYPE: PRT
<213> ORGANISM: Artificial Sequence
<220> FEATURE:
<223> OTHER INFORMATION: spacer sequence, CD2 ectodomain

<400> SEQUENCE: 7

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185
```

<210> SEQ ID NO 8
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 8

```
Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr Val Lys Phe Thr Ser
    50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
        115                 120                 125

Pro Tyr Thr Ser Ser Ser Pro Ile Leu Ser Asp Ile Lys Ala Glu Ile
    130                 135                 140

Lys Cys Ser Gly Ile Arg Glu Val Lys Leu Thr Gln Gly Ile Cys Leu
145                 150                 155                 160

Glu Gln Asn Lys Thr Ser Ser Cys Ala Glu Phe Lys Lys Asp Arg Gly
                165                 170                 175

Glu Gly Leu Ala Arg Val Leu Cys Gly Glu Glu Gln Ala Asp Ala Asp
            180                 185                 190

Ala Gly Ala Gln Val Cys Ser Leu Leu Leu Ala Gln Ser Glu Val Arg
        195                 200                 205

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Lys Leu Gly
225                 230                 235                 240

Ile Leu Asp Phe Thr Glu Gln Asp Val Ala Ser His Gln Ser Tyr Ser
                245                 250                 255

Gln Lys Thr
```

<210> SEQ ID NO 9
<211> LENGTH: 140
<212> TYPE: PRT
<213> ORGANISM: Artificial Sequence
<220> FEATURE:
<223> OTHER INFORMATION: comprising CD28 transmembrane domain and CD3 Z endodomain

<400> SEQUENCE: 9

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Arg Val Lys Phe
            20                  25                  30

Ser Arg Ser Ala Asp Ala Pro Ala Tyr Gln Gln Gly Gln Asn Gln Leu
        35                  40                  45
```

```
Tyr Asn Glu Leu Asn Leu Gly Arg Arg Glu Tyr Asp Val Leu Asp
 50                  55                  60

Lys Arg Arg Gly Arg Asp Pro Glu Met Gly Gly Lys Pro Arg Lys
 65                  70                  75                  80

Asn Pro Gln Glu Gly Leu Tyr Asn Glu Leu Gln Lys Asp Lys Met Ala
                 85                  90                  95

Glu Ala Tyr Ser Glu Ile Gly Met Lys Gly Glu Arg Arg Arg Gly Lys
                100                 105                 110

Gly His Asp Gly Leu Tyr Gln Gly Leu Ser Thr Ala Thr Lys Asp Thr
                115                 120                 125

Tyr Asp Ala Leu His Met Gln Ala Leu Pro Pro Arg
130                 135                 140
```

<210> SEQ ID NO 10
<211> LENGTH: 180
<212> TYPE: PRT
<213> ORGANISM: Artificial Sequence
<220> FEATURE:
<223> OTHER INFORMATION: comprising CD28 transmembrane domain and CD28
      and CD3 Zeta endodomains

<400> SEQUENCE: 10

```
Phe Trp Val Leu Val Val Val Gly Gly Val Leu Ala Cys Tyr Ser Leu
 1               5                  10                  15

Leu Val Thr Val Ala Phe Ile Ile Phe Trp Val Arg Ser Lys Arg Ser
                 20                  25                  30

Arg Leu Leu His Ser Asp Tyr Met Asn Met Thr Pro Arg Arg Pro Gly
                 35                  40                  45

Pro Thr Arg Lys His Tyr Gln Pro Tyr Ala Pro Pro Arg Asp Phe Ala
 50                  55                  60

Ala Tyr Arg Ser Arg Val Lys Phe Ser Arg Ser Ala Asp Ala Pro Ala
 65                  70                  75                  80

Tyr Gln Gln Gly Gln Asn Gln Leu Tyr Asn Glu Leu Asn Leu Gly Arg
                 85                  90                  95

Arg Glu Glu Tyr Asp Val Leu Asp Lys Arg Arg Gly Arg Asp Pro Glu
                100                 105                 110

Met Gly Gly Lys Pro Arg Arg Lys Asn Pro Gln Glu Gly Leu Tyr Asn
                115                 120                 125

Glu Leu Gln Lys Asp Lys Met Ala Glu Ala Tyr Ser Glu Ile Gly Met
130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180
```

<210> SEQ ID NO 11
<211> LENGTH: 216
<212> TYPE: PRT
<213> ORGANISM: Artificial Sequence
<220> FEATURE:
<223> OTHER INFORMATION: comprising CD28 transmembrane domain and CD28,
      OX40 and CD3 Zeta endodomains

<400> SEQUENCE: 11

Phe Trp Val Leu Val Val Gly Gly Val Leu Ala Cys Tyr Ser Leu
1               5                   10                  15
Leu Val Thr Val Ala Phe Ile Ile Phe Trp Val Arg Ser Lys Arg Ser
            20                  25                  30
Arg Leu Leu His Ser Asp Tyr Met Asn Met Thr Pro Arg Arg Pro Gly
        35                  40                  45
Pro Thr Arg Lys His Tyr Gln Pro Tyr Ala Pro Arg Asp Phe Ala
    50                  55                  60
Ala Tyr Arg Ser Arg Asp Gln Arg Leu Pro Pro Asp Ala His Lys Pro
65                  70                  75                  80
Pro Gly Gly Gly Ser Phe Arg Thr Pro Ile Gln Glu Glu Gln Ala Asp
                85                  90                  95
Ala His Ser Thr Leu Ala Lys Ile Arg Val Lys Phe Ser Arg Ser Ala
            100                 105                 110
Asp Ala Pro Ala Tyr Gln Gln Gly Gln Asn Gln Leu Tyr Asn Glu Leu
        115                 120                 125
Asn Leu Gly Arg Arg Glu Glu Tyr Asp Val Leu Asp Lys Arg Arg Gly
    130                 135                 140
Arg Asp Pro Glu Met Gly Gly Lys Pro Arg Arg Lys Asn Pro Gln Glu
145                 150                 155                 160
Gly Leu Tyr Asn Glu Leu Gln Lys Asp Lys Met Ala Glu Ala Tyr Ser
                165                 170                 175
Glu Ile Gly Met Lys Gly Glu Arg Arg Arg Gly Lys Gly His Asp Gly
            180                 185                 190
Leu Tyr Gln Gly Leu Ser Thr Ala Thr Lys Asp Thr Tyr Asp Ala Leu
        195                 200                 205
His Met Gln Ala Leu Pro Pro Arg
    210                 215

<210> SEQ ID NO 12
<211> LENGTH: 20
<212> TYPE: PRT
<213> ORGANISM: Artificial Sequence
<220> FEATURE:
<223> OTHER INFORMATION: 2A-like sequence

<400> SEQUENCE: 12

Arg Ala Glu Gly Arg Gly Ser Leu Leu Thr Cys Gly Asp Val Glu Glu
1               5                   10                  15
Asn Pro Gly Pro
            20

<210> SEQ ID NO 13
<211> LENGTH: 3402
<212> TYPE: DNA
<213> ORGANISM: Artificial Sequence
<220> FEATURE:
<223> OTHER INFORMATION: CD19/CD22 'OR' gate construct

<400> SEQUENCE: 13
atgagcctgc ccgtgaccgc cctgctgctg cccctggccc tgctgctgca cgccgccaga      60
ccatacccct acgacgtgcc cgactacgcc agcctgagcg aggcggcgg cagccaggtg     120 cagctggtgc agagcggagc cgaggtgaag aagcctggcg ccagcgtgaa ggtgtcctgt     180
aaggccagcg gctacacctt caccagcaac tggatgcact gggtgaggca ggcccctgga     240
cagggactgg agtggatggg cgagatcgac cccagcgaca gctacaccaa ctacaaccag     300

```
aagttcaagg gccgggtgac catcaccgtg ataagagcg ccagcaccgc ctacatggag      360
ctgtccagcc tgagaagcga ggataccgcc gtgtactact gtgccagagg cagcaacccc      420
tactactacg ctatggacta ctggggccag ggcaccctgg tgaccgtgtc cagcggcgga      480
ggaggaagcg gaggggcgg atctggcggc ggagggagcg agatcgtgct gacccagagc      540
cccgccaccc tgagcctgag ccctggcgag agagccaccc tgtcctgtag cgccagcagc      600
ggcgtgaatt acatgcactg gtatcagcag aagcccggcc aggcccccag aagatggatc      660
tacgacacca gcaagctggc cagcggcgtg cccgccagat tcagcggcag cggctccggc      720
accagctaca gcctgaccat cagcagcctg gagcctgagg atttcgccgt gtattattgc      780
caccagaggg gcagctacac ctttggcggc ggaacaaagc tggagatcaa gcgctcagat      840
cccaccacga cgccagcgcc gcgaccacca acaccggcgc ccaccatcgc gtcgcagccc      900
ctgtccctgc gcccagaggc gtgccggcca gcggcggggg gcgcagtgca cacgaggggg      960
ctggacttcg cctgtgatat cttttgggtg ctggtggtgg ttggtggagt cctggcttgc     1020
tatagcttgc tagtaacagt ggcctttatt attttctggg tgaggagagt gaagttcagc     1080
aggagcgcag acgccccgc gtaccagcag ggccagaacc agctctataa cgagctcaat     1140
ctaggacgaa gagaggagta cgatgttttg acaagagac gtggccggga ccctgagatg     1200 ggggaaagc cgagaaggaa gaaccctcag gaaggcctgt acaatgaact gcagaaagat     1260 aagatggcg aggcctacag tgagattggg atgaaaggcg agcgccggag gggcaagggg     1320
cacgatggcc tttaccaggg tctcagtaca gccaccaagg acacctacga cgcccttcac     1380
atgcaggccc tgcctcctcg cagagccgag ggcaggggaa gtcttctaac atgcggggac     1440
gtggaggaaa atcccgggcc catggagttt gggctgagct ggcttttct tgtggctatt     1500 ttaaaaggtg tccagtgcga ggtgcagctg gtggagtctg ggggaggctt ggtccagcca     1560 gggggtccc tgcgcctctc ctgtgcagcc tctggattcg ctttcagtat ctatgacatg     1620
tcttgggtcc gccaggttcc ggggaagggg ctggagtggg tctcatatat tagtagtggt     1680
ggtggtacca cctattaccc ggacactgtg aagggccgct tcaccatctc ccgtgacaat     1740
tcccgcaaca ctctggatct tcaaatgaac agtctgcgcg tcgaggacac ggctgtctat     1800
tattgtgcgc gtcatagtgg ctacggtagt agctacgggg ttttgtttgc ttactggggc     1860
caaggaaccc tggtcaccgt ctcctcaggt ggaggcggtt caggcggagg tggctctggc     1920
ggtggcggat cggacatcca gatgactcag tctccgtcct ccctgtctgc atctgtagga     1980
gaccgcgtca ccatcacctg ccgtgcaagt caggacatta gcaattattt aaactggctt     2040
caacagaaac cggggaaagc cccgaagctc ctgatttact acacatcaat cttacactca     2100
ggagtcccgt cacgcttcag cggcagtgga tctgggacag aattcactct cacaatcagc     2160
agcctgcagc cggaagattt tgcaacttat tactgtcaac agggtaatac gcttccgtgg     2220
acgtttggcc aggggaccaa actggaaatc aaacgttcgg atccagccga accaaagagc     2280
cccgataaga cccacacctg tccccctgc ccagccccag agctgctggg aggcccagc     2340 gtgtttctgt tccacccaa gccaaaggat accctgatga ttagtagaac acccgaagtg     2400
acctgtgtgg tggtggatgt gtctcacgag gaccccgagt tgaaatttaa ttggtatgtt     2460
gatggtgttg aagtgcacaa cgccaaaacc aaacccagag aggagcagta caattctacc     2520
tatagagtcg tgtctgtgct gacagtgctg catcaggatt ggctgaacgg aaaagaatac     2580
aaatgtaaag tgagcaataa ggccctgccc gctccaattg agaagacaat tagcaaggcc     2640
aagggccagc caagggagcc ccaggtgtat acactgccac ccagtagaga cgaactgaca     2700
```

```
aagaatcagg tgtctctgac atgtctggtg aagggatttt acccatctga tatcgccgtg    2760
gaatgggaat ctaacggcca gcccgagaat aactataaga caaccccacc agtgctggat    2820
agcgatggca gcttttttct gtattctaag ctgacagtgg ataagtcccg gtggcagcag    2880
ggaaatgtgt ttagctgtag tgtcatgcat gaggccctgc acaatcacta tacccagaaa    2940
tctctgagtc tgagcccagg caagaaggac cccaagttct gggtcctggt ggtggtggga    3000
ggcgtgctgg cctgttactc tctcctggtg accgtggcct tcatcatctt ttgggtcgcc    3060
tcccgggtga gttttctcg ctctgccgat gccccagcct atcagcaggg ccagaatcag    3120
ctgtacaatg aactgaacct gggcaggcgg gaggagtacg acgtgctgga taagcggaga    3180
ggcagagacc ccgagatggg cggcaaacca cggcgcaaaa atccccagga gggactctat    3240
aacgagctgc agaaggacaa aatggccgag gcctattccg agatcggcat gaagggagag    3300
agaagacgcg gaaagggcca cgacggcctg tatcagggat tgtccaccgc tacaaaagat    3360
acatatgatg ccctgcacat gcaggccctg ccacccagat ga    3402
```

<210> SEQ ID NO 14
<211> LENGTH: 1133
<212> TYPE: PRT
<213> ORGANISM: Artificial Sequence
<220> FEATURE:
<223> OTHER INFORMATION: CD19/CD22 'OR' gate construct

<400> SEQUENCE: 14

```
Met Ser Leu Pro Val Thr Ala Leu Leu Leu Pro Leu Ala Leu Leu Leu
1               5                   10                  15

His Ala Ala Arg Pro Tyr Pro Tyr Asp Val Pro Asp Tyr Ala Ser Leu
            20                  25                  30

Ser Gly Gly Gly Gly Ser Gln Val Gln Leu Val Gln Ser Gly Ala Glu
        35                  40                  45

Val Lys Lys Pro Gly Ala Ser Val Lys Val Ser Cys Lys Ala Ser Gly
    50                  55                  60

Tyr Thr Phe Thr Ser Asn Trp Met His Trp Val Arg Gln Ala Pro Gly
65                  70                  75                  80

Gln Gly Leu Glu Trp Met Gly Glu Ile Asp Pro Ser Asp Ser Tyr Thr
                85                  90                  95

Asn Tyr Asn Gln Lys Phe Lys Gly Arg Val Thr Ile Thr Val Asp Lys
            100                 105                 110

Ser Ala Ser Thr Ala Tyr Met Glu Leu Ser Ser Leu Arg Ser Glu Asp
        115                 120                 125

Thr Ala Val Tyr Tyr Cys Ala Arg Gly Ser Asn Pro Tyr Tyr Tyr Ala
    130                 135                 140

Met Asp Tyr Trp Gly Gln Gly Thr Leu Val Thr Val Ser Ser Gly Gly
145                 150                 155                 160

Gly Gly Ser Gly Gly Gly Gly Ser Gly Gly Gly Gly Ser Glu Ile Val
                165                 170                 175

Leu Thr Gln Ser Pro Ala Thr Leu Ser Leu Ser Pro Gly Glu Arg Ala
            180                 185                 190

Thr Leu Ser Cys Ser Ala Ser Ser Gly Val Asn Tyr Met His Trp Tyr
        195                 200                 205

Gln Gln Lys Pro Gly Gln Ala Pro Arg Arg Trp Ile Tyr Asp Thr Ser
    210                 215                 220

Lys Leu Ala Ser Gly Val Pro Ala Arg Phe Ser Gly Ser Gly Ser Gly
225                 230                 235                 240
```

-continued

```
Thr Ser Tyr Ser Leu Thr Ile Ser Ser Leu Glu Pro Glu Asp Phe Ala
            245                 250                 255

Val Tyr Tyr Cys His Gln Arg Gly Ser Tyr Thr Phe Gly Gly Gly Thr
        260                 265                 270

Lys Leu Glu Ile Lys Arg Ser Asp Pro Thr Thr Thr Pro Ala Pro Arg
    275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Phe Trp Val Leu Val Val Val Gly Gly
                325                 330                 335

Val Leu Ala Cys Tyr Ser Leu Leu Val Thr Val Ala Phe Ile Ile Phe
            340                 345                 350

Trp Val Arg Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460

Pro Pro Arg Arg Ala Glu Gly Arg Gly Ser Leu Leu Thr Cys Gly Asp
465                 470                 475                 480

Val Glu Glu Asn Pro Gly Pro Met Glu Phe Gly Leu Ser Trp Leu Phe
                485                 490                 495

Leu Val Ala Ile Leu Lys Gly Val Gln Cys Glu Val Gln Leu Val Glu
            500                 505                 510

Ser Gly Gly Gly Leu Val Gln Pro Gly Gly Ser Leu Arg Leu Ser Cys
        515                 520                 525

Ala Ala Ser Gly Phe Ala Phe Ser Ile Tyr Asp Met Ser Trp Val Arg
    530                 535                 540

Gln Val Pro Gly Lys Gly Leu Glu Trp Val Ser Tyr Ile Ser Ser Gly
545                 550                 555                 560

Gly Gly Thr Thr Tyr Tyr Pro Asp Thr Val Lys Gly Arg Phe Thr Ile
                565                 570                 575

Ser Arg Asp Asn Ser Arg Asn Thr Leu Asp Leu Gln Met Asn Ser Leu
            580                 585                 590

Arg Val Glu Asp Thr Ala Val Tyr Tyr Cys Ala Arg His Ser Gly Tyr
        595                 600                 605

Gly Ser Ser Tyr Gly Val Leu Phe Ala Tyr Trp Gly Gln Gly Thr Leu
    610                 615                 620

Val Thr Val Ser Ser Gly Gly Gly Gly Ser Gly Gly Gly Gly Ser Gly
625                 630                 635                 640

Gly Gly Gly Ser Asp Ile Gln Met Thr Gln Ser Pro Ser Ser Leu Ser
                645                 650                 655
```

```
Ala Ser Val Gly Asp Arg Val Thr Ile Thr Cys Arg Ala Ser Gln Asp
            660                 665                 670

Ile Ser Asn Tyr Leu Asn Trp Leu Gln Gln Lys Pro Gly Lys Ala Pro
        675                 680                 685

Lys Leu Leu Ile Tyr Tyr Thr Ser Ile Leu His Ser Gly Val Pro Ser
    690                 695                 700

Arg Phe Ser Gly Ser Gly Ser Gly Thr Glu Phe Thr Leu Thr Ile Ser
705                 710                 715                 720

Ser Leu Gln Pro Glu Asp Phe Ala Thr Tyr Tyr Cys Gln Gln Gly Asn
                725                 730                 735

Thr Leu Pro Trp Thr Phe Gly Gln Gly Thr Lys Leu Glu Ile Lys Arg
            740                 745                 750

Ser Asp Pro Ala Glu Pro Lys Ser Pro Asp Lys Thr His Thr Cys Pro
        755                 760                 765

Pro Cys Pro Ala Pro Glu Leu Leu Gly Gly Pro Ser Val Phe Leu Phe
    770                 775                 780

Pro Pro Lys Pro Lys Asp Thr Leu Met Ile Ser Arg Thr Pro Glu Val
785                 790                 795                 800

Thr Cys Val Val Val Asp Val Ser His Glu Asp Pro Glu Val Lys Phe
                805                 810                 815

Asn Trp Tyr Val Asp Gly Val Glu Val His Asn Ala Lys Thr Lys Pro
            820                 825                 830

Arg Glu Glu Gln Tyr Asn Ser Thr Tyr Arg Val Val Ser Val Leu Thr
        835                 840                 845

Val Leu His Gln Asp Trp Leu Asn Gly Lys Glu Tyr Lys Cys Lys Val
    850                 855                 860

Ser Asn Lys Ala Leu Pro Ala Pro Ile Glu Lys Thr Ile Ser Lys Ala
865                 870                 875                 880

Lys Gly Gln Pro Arg Glu Pro Gln Val Tyr Thr Leu Pro Pro Ser Arg
                885                 890                 895

Asp Glu Leu Thr Lys Asn Gln Val Ser Leu Thr Cys Leu Val Lys Gly
            900                 905                 910

Phe Tyr Pro Ser Asp Ile Ala Val Glu Trp Glu Ser Asn Gly Gln Pro
        915                 920                 925

Glu Asn Asn Tyr Lys Thr Thr Pro Pro Val Leu Asp Ser Asp Gly Ser
    930                 935                 940

Phe Phe Leu Tyr Ser Lys Leu Thr Val Asp Lys Ser Arg Trp Gln Gln
945                 950                 955                 960

Gly Asn Val Phe Ser Cys Ser Val Met His Glu Ala Leu His Asn His
                965                 970                 975

Tyr Thr Gln Lys Ser Leu Ser Leu Ser Pro Gly Lys Lys Asp Pro Lys
            980                 985                 990

Phe Trp Val Leu Val Val Val Gly Gly Val Leu Ala Cys Tyr Ser Leu
        995                 1000                1005

Leu Val Thr Val Ala Phe Ile Ile Phe Trp Val Arg Ser Arg Val
    1010                1015                1020

Lys Phe Ser Arg Ser Ala Asp Ala Pro Ala Tyr Gln Gln Gly Gln
    1025                1030                1035

Asn Gln Leu Tyr Asn Glu Leu Asn Leu Gly Arg Arg Glu Glu Tyr
    1040                1045                1050

Asp Val Leu Asp Lys Arg Arg Gly Arg Asp Pro Glu Met Gly Gly
    1055                1060                1065
```

Lys Pro Arg Arg Lys Asn Pro Gln Glu Gly Leu Tyr Asn Glu Leu
    1070                1075                1080

Gln Lys Asp Lys Met Ala Glu Ala Tyr Ser Glu Ile Gly Met Lys
    1085                1090                1095

Gly Glu Arg Arg Arg Gly Lys Gly His Asp Gly Leu Tyr Gln Gly
    1100                1105                1110

Leu Ser Thr Ala Thr Lys Asp Thr Tyr Asp Ala Leu His Met Gln
    1115                1120                1125

Ala Leu Pro Pro Arg
    1130

<210> SEQ ID NO 15
<211> LENGTH: 5
<212> TYPE: PRT
<213> ORGANISM: Artificial Sequence
<220> FEATURE:
<223> OTHER INFORMATION: Complementarity determining region (CDR)
      variable heavy chain (VH) CDR1

<400> SEQUENCE: 15

Ser Tyr Trp Met Asn
1               5

<210> SEQ ID NO 16
<211> LENGTH: 16
<212> TYPE: PRT
<213> ORGANISM: Artificial Sequence
<220> FEATURE:
<223> OTHER INFORMATION: VH CDR2

<400> SEQUENCE: 16

Gln Ile Trp Pro Gly Asp Gly Asp Thr Asn Tyr Asn Gly Lys Phe Lys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: VH CDR3

<400> SEQUENCE: 17

Arg Glu Thr Thr Thr Val Gly Arg Tyr Tyr Tyr Ala Met Asp Tyr
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Variable light chain (VL) CDR1

<400> SEQUENCE: 18

Lys Ala Ser Gln Ser Val Asp Tyr Asp Gly Asp Ser Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: VL CDR2

```
<400> SEQUENCE: 19

Asp Ala Ser Asn Leu Val Ser
1               5

<210> SEQ ID NO 20
<211> LENGTH: 9
<212> TYPE: PRT
<213> ORGANISM: Artificial Sequence
<220> FEATURE:
<223> OTHER INFORMATION: VL CDR3

<400> SEQUENCE: 20

Gln Gln Ser Thr Glu Asp Pro Trp Thr
1               5

<210> SEQ ID NO 21
<211> LENGTH: 235
<212> TYPE: PRT
<213> ORGANISM: Artificial Sequence
<220> FEATURE:
<223> OTHER INFORMATION: chimeric antigen receptor (CAR), Murine
      CD19ALAb scFv sequence

<400> SEQUENCE: 21

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Asp Ile Gln Leu
        115                 120                 125

Thr Gln Ser Pro Ala Ser Leu Ala Val Ser Leu Gly Gln Arg Ala Thr
    130                 135                 140

Ile Ser Cys Lys Ala Ser Gln Ser Val Asp Tyr Asp Gly Asp Ser Tyr
145                 150                 155                 160

Leu Asn Trp Tyr Gln Gln Ile Pro Gly Gln Pro Pro Lys Leu Leu Ile
                165                 170                 175

Tyr Asp Ala Ser Asn Leu Val Ser Gly Ile Pro Pro Arg Phe Ser Gly
            180                 185                 190

Ser Gly Ser Gly Thr Asp Phe Thr Leu Asn Ile His Pro Val Glu Lys
        195                 200                 205

Val Asp Ala Ala Thr Tyr His Cys Gln Gln Ser Thr Glu Asp Pro Trp
    210                 215                 220

Thr Phe Gly Gly Gly Thr Lys Leu Glu Ile Lys
225                 230                 235

<210> SEQ ID NO 22
<211> LENGTH: 236
<212> TYPE: PRT
<213> ORGANISM: Artificial Sequence
```

```
<220> FEATURE:
<223> OTHER INFORMATION: CAR, Humanised CD19ALAb scFv sequence - Heavy
      19, Kappa 16

<400> SEQUENCE: 22

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
                20                  25                  30

Trp Met Asn Trp Val Arg Gln Ala Pro Gly Gln Ser Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Lys Gly Thr Leu Val Thr Val Ser Ser Asp Ile Gln Leu
            115                 120                 125

Thr Gln Ser Pro Asp Ser Leu Ala Val Ser Leu Gly Glu Arg Ala Thr
        130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Leu Leu Ile
                165                 170                 175

Tyr Asp Ala Ser Asn Leu Val Ser Gly Val Pro Asp Arg Phe Ser Gly
            180                 185                 190

Ser Gly Ser Gly Thr Asp Phe Thr Leu Thr Ile Ser Ser Leu Gln Ala
        195                 200                 205

Ala Asp Val Ala Val Tyr His Cys Gln Gln Ser Thr Glu Asp Pro Trp
    210                 215                 220

Thr Phe Gly Gln Gly Thr Lys Val Glu Ile Lys Arg
225                 230                 235

<210> SEQ ID NO 23
<211> LENGTH: 124
<212> TYPE: PRT
<213> ORGANISM: Artificial Sequence
<220> FEATURE:
<223> OTHER INFORMATION: CAR, Murine CD19ALAb VH sequence

<400> SEQUENCE: 23

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95
```

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 24
<211> LENGTH: 124
<212> TYPE: PRT
<213> ORGANISM: Artificial Sequence
<220> FEATURE:
<223> OTHER INFORMATION: CAR, Humanised CD19ALAb VH sequence

<400> SEQUENCE: 24

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
            20                  25                  30

Trp Met Asn Trp Val Arg Gln Ala Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Lys Gly Thr Leu Val Thr Val Ser Ser
        115                 120

<210> SEQ ID NO 25
<211> LENGTH: 111
<212> TYPE: PRT
<213> ORGANISM: Artificial Sequence
<220> FEATURE:
<223> OTHER INFORMATION: CAR, Murine CD19ALAb VL sequence

<400> SEQUENCE: 25

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: CAR, Humanised CD19ALAb VL sequence, Kappa16

```
<400> SEQUENCE: 26

Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
            35                  40                  45

Lys Leu Leu Ile Tyr Ala Ser Asn Leu Val Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Ala Asp Val Ala Val Tyr His Cys Gln Gln Ser Thr
                85                  90                  95

Glu Asp Pro Trp Thr Phe Gly Gln Gly Thr Lys Val Glu Ile Lys Arg
                100                 105                 110

<210> SEQ ID NO 27
<211> LENGTH: 5
<212> TYPE: PRT
<213> ORGANISM: Artificial Sequence
<220> FEATURE:
<223> OTHER INFORMATION: VH CDR1

<400> SEQUENCE: 27

Asn Tyr Trp Ile Asn
1               5

<210> SEQ ID NO 28
<211> LENGTH: 17
<212> TYPE: PRT
<213> ORGANISM: Artificial Sequence
<220> FEATURE:
<223> OTHER INFORMATION: VH CDR2

<400> SEQUENCE: 28

Asn Ile Tyr Pro Ser Asp Ser Phe Thr Asn Tyr Asn Gln Lys Phe Lys
1               5                   10                  15

Asp

<210> SEQ ID NO 29
<211> LENGTH: 11
<212> TYPE: PRT
<213> ORGANISM: Artificial Sequence
<220> FEATURE:
<223> OTHER INFORMATION: VH CDR3

<400> SEQUENCE: 29

Asp Thr Gln Glu Arg Ser Trp Tyr Phe Asp Val
1               5                   10

<210> SEQ ID NO 30
<211> LENGTH: 16
<212> TYPE: PRT
<213> ORGANISM: Artificial Sequence
<220> FEATURE:
<223> OTHER INFORMATION: VL CDR1

<400> SEQUENCE: 30

Arg Ser Ser Gln Ser Leu Val His Ser Asn Gly Asn Thr Tyr Leu His
1               5                   10                  15
```

```
<210> SEQ ID NO 31
<211> LENGTH: 7
<212> TYPE: PRT
<213> ORGANISM: Artificial Sequence
<220> FEATURE:
<223> OTHER INFORMATION: VL CDR2

<400> SEQUENCE: 31

Lys Val Ser Asn Arg Phe Ser
1               5

<210> SEQ ID NO 32
<211> LENGTH: 9
<212> TYPE: PRT
<213> ORGANISM: Artificial Sequence
<220> FEATURE:
<223> OTHER INFORMATION: VL CDR3

<400> SEQUENCE: 32

Ser Gln Ser Thr His Val Pro Trp Thr
1               5

<210> SEQ ID NO 33
<211> LENGTH: 232
<212> TYPE: PRT
<213> ORGANISM: Artificial Sequence
<220> FEATURE:
<223> OTHER INFORMATION: CAR, Murine CD22ALAb scFv sequence

<400> SEQUENCE: 33

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Phe Thr Asn Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Asp Thr Gln Glu Arg Ser Trp Tyr Phe Asp Val Trp Gly Ala
            100                 105                 110

Gly Thr Thr Val Thr Val Ser Ser Asp Val Val Met Thr Gln Thr Pro
        115                 120                 125

Leu Ser Leu Pro Val Ser Leu Gly Asp Gln Ala Ser Ile Ser Cys Arg
    130                 135                 140

Ser Ser Gln Ser Leu Val His Ser Asn Gly Asn Thr Tyr Leu His Trp
145                 150                 155                 160

Tyr Leu Gln Lys Pro Gly Gln Ser Pro Lys Leu Leu Ile Tyr Lys Val
                165                 170                 175

Ser Asn Arg Phe Ser Gly Val Pro Asp Arg Phe Ser Gly Ser Gly Ser
            180                 185                 190

Gly Thr Asp Phe Thr Leu Lys Ile Ser Arg Val Glu Ala Glu Asp Leu
        195                 200                 205

Gly Leu Tyr Phe Cys Ser Gln Ser Thr His Val Pro Trp Thr Phe Gly
    210                 215                 220

Gly Gly Thr Lys Leu Glu Ile Lys
225                 230
```

<210> SEQ ID NO 34
<211> LENGTH: 232
<212> TYPE: PRT
<213> ORGANISM: Artificial Sequence
<220> FEATURE:
<223> OTHER INFORMATION: CAR, Humanised CD22ALAb scFv sequence

<400> SEQUENCE: 34

```
Glu Val Gln Leu Val Glu Ser Gly Ala Glu Val Lys Pro Gly Ser
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Asp Ser Phe Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Leu Glu Leu Arg Asn Leu Arg Ser Asp Asp Thr Ala Val Tyr Tyr Cys
                85                  90                  95

Thr Arg Asp Thr Gln Glu Arg Ser Trp Tyr Phe Asp Val Trp Gly Gln
            100                 105                 110

Gly Thr Leu Val Thr Val Ser Ser Asp Ile Val Met Thr Gln Ser Pro
        115                 120                 125

Ala Thr Leu Ser Val Ser Pro Gly Glu Arg Ala Thr Leu Ser Cys Arg
    130                 135                 140

Ser Ser Gln Ser Leu Val His Ser Asn Gly Asn Thr Tyr Leu His Trp
145                 150                 155                 160

Tyr Gln Gln Lys Pro Gly Gln Ala Pro Arg Leu Leu Ile Tyr Lys Val
                165                 170                 175

Ser Asn Arg Phe Ser Gly Val Pro Ala Arg Phe Ser Gly Ser Gly Ser
            180                 185                 190

Gly Val Glu Phe Thr Leu Thr Ile Ser Ser Leu Gln Ser Glu Asp Phe
        195                 200                 205

Ala Val Tyr Tyr Cys Ser Gln Ser Thr His Val Pro Trp Thr Phe Gly
    210                 215                 220

Gln Gly Thr Arg Leu Glu Ile Lys
225                 230
```

<210> SEQ ID NO 35
<211> LENGTH: 120
<212> TYPE: PRT
<213> ORGANISM: Artificial Sequence
<220> FEATURE:
<223> OTHER INFORMATION: CAR, Murine CD22ALAb VH sequence

<400> SEQUENCE: 35

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Phe Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80
```

```
Met Gln Leu Ser Ser Pro Thr Ser Glu Asp Ser Ala Val Tyr Tyr Cys
            85                  90                  95

Thr Arg Asp Thr Gln Glu Arg Ser Trp Tyr Phe Asp Val Trp Gly Ala
        100                 105                 110

Gly Thr Thr Val Thr Val Ser Ser
        115                 120
```

<210> SEQ ID NO 36
<211> LENGTH: 120
<212> TYPE: PRT
<213> ORGANISM: Artificial Sequence
<220> FEATURE:
<223> OTHER INFORMATION: CAR, Humanised CD22ALAb VH sequence

<400> SEQUENCE: 36

```
Glu Val Gln Leu Val Glu Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Asp Ser Phe Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Leu Glu Leu Arg Asn Leu Arg Ser Asp Thr Ala Val Tyr Tyr Cys
            85                  90                  95

Thr Arg Asp Thr Gln Glu Arg Ser Trp Tyr Phe Asp Val Trp Gly Gln
        100                 105                 110

Gly Thr Leu Val Thr Val Ser Ser
        115                 120
```

<210> SEQ ID NO 37
<211> LENGTH: 112
<212> TYPE: PRT
<213> ORGANISM: Artificial Sequence
<220> FEATURE:
<223> OTHER INFORMATION: CAR, Murine CD22ALAb VL sequence

<400> SEQUENCE: 37

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
            85                  90                  95

Thr His Val Pro Trp Thr Phe Gly Gly Gly Thr Lys Leu Glu Ile Lys
        100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: CAR, Humanised CD22ALAb VL sequence

<400> SEQUENCE: 38

Asp Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Ala Arg Phe Ser Gly Ser Gly Ser Gly Val Glu Phe Thr Leu Thr Ile
65                  70                  75                  80

Ser Ser Leu Gln Ser Glu Asp Phe Ala Val Tyr Tyr Cys Ser Gln Ser
                85                  90                  95

Thr His Val Pro Trp Thr Phe Gly Gln Gly Thr Arg Leu Glu Ile Lys
            100                 105                 110

<210> SEQ ID NO 39
<211> LENGTH: 236
<212> TYPE: PRT
<213> ORGANISM: Artificial Sequence
<220> FEATURE:
<223> OTHER INFORMATION: CAR, Humanised CD19ALAb scFv sequence - Heavy
      19, Kappa 7

<400> SEQUENCE: 39

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
            20                  25                  30

Trp Met Asn Trp Val Arg Gln Ala Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Lys Gly Thr Leu Val Thr Val Ser Ser Asp Ile Gln Leu
        115                 120                 125

Thr Gln Ser Pro Asp Ser Leu Ala Val Ser Leu Gly Glu Arg Ala Thr
    130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Val Leu Ile
                165                 170                 175

Tyr Asp Ala Ser Asn Leu Val Ser Gly Val Pro Asp Arg Phe Ser Gly
            180                 185                 190

Ser Gly Ser Gly Thr Asp Phe Thr Leu Thr Ile Ser Ser Leu Gln Ala
        195                 200                 205

```
Ala Asp Val Ala Val Tyr Tyr Cys Gln Gln Ser Thr Glu Asp Pro Trp
    210                 215                 220

Thr Phe Gly Gln Gly Thr Lys Val Glu Ile Lys Arg
225                 230                 235

<210> SEQ ID NO 40
<211> LENGTH: 112
<212> TYPE: PRT
<213> ORGANISM: Artificial Sequence
<220> FEATURE:
<223> OTHER INFORMATION: CAR, Humanised CD19ALAb VL sequence, Kappa 7

<400> SEQUENCE: 40

Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Val Leu Ile Tyr Asp Ala Ser Asn Leu Val Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Ala Asp Val Ala Val Tyr Tyr Cys Gln Gln Ser Thr
                85                  90                  95

Glu Asp Pro Trp Thr Phe Gly Gln Gly Thr Lys Val Glu Ile Lys Arg
            100                 105                 110

<210> SEQ ID NO 41
<211> LENGTH: 40
<212> TYPE: PRT
<213> ORGANISM: Artificial Sequence
<220> FEATURE:
<223> OTHER INFORMATION: CD28 co-stimulatory endodomain

<400> SEQUENCE: 41

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 42
<211> LENGTH: 36
<212> TYPE: PRT
<213> ORGANISM: Artificial Sequence
<220> FEATURE:
<223> OTHER INFORMATION: OX40 endodomain

<400> SEQUENCE: 42

Arg Asp Gln Arg Leu Pro Pro Asp Ala His Lys Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35
```

```
<210> SEQ ID NO 43
<211> LENGTH: 42
<212> TYPE: PRT
<213> ORGANISM: Artificial Sequence
<220> FEATURE:
<223> OTHER INFORMATION: 4-1BB endodomain

<400> SEQUENCE: 43

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 44
<211> LENGTH: 112
<212> TYPE: PRT
<213> ORGANISM: Artificial Sequence
<220> FEATURE:
<223> OTHER INFORMATION: CD3zeta endodomain

<400> SEQUENCE: 44

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 45
<211> LENGTH: 24
<212> TYPE: PRT
<213> ORGANISM: Artificial Sequence
<220> FEATURE:
<223> OTHER INFORMATION: Tyrp-1 transmembrane sequence

<400> SEQUENCE: 45

Ile Ile Ala Ile Ala Val Val Gly Ala Leu Leu Leu Val Ala Leu Ile
1               5                   10                  15

Phe Gly Thr Ala Ser Tyr Leu Ile
            20

<210> SEQ ID NO 46
<211> LENGTH: 258
<212> TYPE: PRT
<213> ORGANISM: Homo sapiens

<400> SEQUENCE: 46

Glu Glu Pro Leu Val Val Lys Val Glu Glu Gly Asp Asn Ala Val Leu
1               5                   10                  15

Gln Cys Leu Lys Gly Thr Ser Asp Gly Pro Thr Gln Gln Leu Thr Trp
            20                  25                  30
```

Ser Arg Glu Ser Pro Leu Lys Pro Phe Leu Lys Leu Ser Leu Gly Leu
        35                  40                  45

Pro Gly Leu Gly Ile His Met Arg Pro Leu Ala Ile Trp Leu Phe Ile
 50                  55                  60

Phe Asn Val Ser Gln Gln Met Gly Gly Phe Tyr Leu Cys Gln Pro Gly
 65                  70                  75                  80

Pro Pro Ser Glu Lys Ala Trp Gln Pro Gly Trp Thr Val Asn Val Glu
                 85                  90                  95

Gly Ser Gly Glu Leu Phe Arg Trp Asn Val Ser Asp Leu Gly Gly Leu
            100                 105                 110

Gly Cys Gly Leu Lys Asn Arg Ser Ser Glu Gly Pro Ser Ser Pro Ser
            115                 120                 125

Gly Lys Leu Met Ser Pro Lys Leu Tyr Val Trp Ala Lys Asp Arg Pro
        130                 135                 140

Glu Ile Trp Glu Gly Glu Pro Pro Cys Leu Pro Arg Asp Ser Leu
145                 150                 155                 160

Asn Gln Ser Leu Ser Gln Asp Leu Thr Met Ala Pro Gly Ser Thr Leu
                165                 170                 175

Trp Leu Ser Cys Gly Val Pro Pro Asp Ser Val Ser Arg Gly Pro Leu
            180                 185                 190

Ser Trp Thr His Val His Pro Lys Gly Pro Lys Ser Leu Leu Ser Leu
        195                 200                 205

Glu Leu Lys Asp Asp Arg Pro Ala Arg Asp Met Trp Val Met Glu Thr
210                 215                 220

Gly Leu Leu Leu Pro Arg Ala Thr Ala Gln Asp Ala Gly Lys Tyr Tyr
225                 230                 235                 240

Cys His Arg Gly Asn Leu Thr Met Ser Phe His Leu Glu Ile Thr Ala
                245                 250                 255

Arg Pro

<210> SEQ ID NO 47
<211> LENGTH: 4
<212> TYPE: PRT
<213> ORGANISM: Artificial Sequence
<220> FEATURE:
<223> OTHER INFORMATION: ITAM motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be leucine or isoleucine

<400> SEQUENCE: 47

Tyr Xaa Xaa Xaa
1

<210> SEQ ID NO 48
<211> LENGTH: 1139
<212> TYPE: DNA
<213> ORGANISM: Homo sapiens

<400> SEQUENCE: 48
atcccgccga gcccaaatct cctgacaaaa ctcacacatg cccaccgtgc ccagcacctg    60
aactcctggg gggaccgtca gtcttcctct tccccccaaa acccaaggac accctcatga   120
tctcccggac ccctgaggtc acatgcgtgg tggtggacgt gagccacgaa gaccctgagg   180

| | |
|---|---|
| tcaagttcaa ctggtacgtg gacggcgtgg aggtgcataa tgccaagaca aagccgcggg | 240 |
| aggagcagta caacagcacg taccgtgtgg tcagcgtcct caccgtcctg caccaggact | 300 |
| ggctgaatgg caaggagtac aagtgcaagg tctccaacaa agccctccca gcccccatcg | 360 |
| agaaaaccat ctccaaagcc aaagggcagc ccgagaacc acaggtgtac accctgcccc | 420 |
| catcccggga tgagctgacc aagaaccagg tcagcctgac ctgcctggtc aaaggcttct | 480 |
| atcccagcga catcgccgtg gagtgggaga gcaatgggca accggagaac aactacaaga | 540 |
| ccacgcctcc cgtgctggac tccgacggct ccttcttcct ctacagcaag ctcaccgtgg | 600 |
| acaagagcag gtggcagcag gggaacgtct tctcatgctc cgtgatgcac gaggctctgc | 660 |
| acaaccacta cacgcagaag agcctctccc tgtctccggg taaaaaagat cccaaatttt | 720 |
| gggtgctggt ggtggttggt ggagtcctgg cttgctatag cttgctagta acagtggcct | 780 |
| ttattatttt ctgggtgagg agagtgaagt tcagcaggag cgcagacgcc cccgcgtacc | 840 |
| agcagggcca gaaccagctc tataacgagc tcaatctagg acgaagagag gagtacgatg | 900 |
| ttttggacaa gagacgtggc cgggaccctg agatgggggg aaagccgaga aggaagaacc | 960 |
| ctcaggaagg cctgtacaat gaactgcaga agataagat ggcggaggcc tacagtgaga | 1020 |
| ttgggatgaa aggcgagcgc cggaggggca aggggcacga tggcctttac cagggtctca | 1080 |
| gtacagccac caaggacacc tacgacgccc ttcacatgca ggccctgcct cctcgcgag | 1139 |

<210> SEQ ID NO 49
<211> LENGTH: 1139
<212> TYPE: DNA
<213> ORGANISM: Artificial Sequence
<220> FEATURE:
<223> OTHER INFORMATION: codon-wobbled HCH2CH3-CD28tmZeta

<400> SEQUENCE: 49

| | |
|---|---|
| atccagccga accaaagagc ccgataagag cccacacctg tcccccctgc ccagccccag | 60 |
| agctgctggg aggccccagc gtgtttctgt ttccacccaa gccaaaggat accctgatga | 120 |
| ttagtagaac acccgaagtg acctgtgtgg tggtggatgt gtctcacgag gaccccgagg | 180 |
| tgaaatttaa ttggtatgtt gatggtgttg aagtgcacaa cgccaaaacc aaacccagag | 240 |
| aggagcagta caattctacc tatagagtcg tgtctgtgct gacagtgctg catcaggatt | 300 |
| ggctgaacgg aaaagaatac aaatgtaaag tgagcaataa ggccctgccc gctccaattg | 360 |
| agaagacaat tagcaaggcc aagggccagc caagggagcc ccaggtgtat acactgccac | 420 |
| ccagtagaga cgaactgaca aagaatcagg tgtctctgac atgtctggtg aagggatttt | 480 |
| acccatctga tatcgccgtg gaatgggaat ctaacggcca gcccgagaat aactataaga | 540 |
| caaccccacc agtgctggat agcgatggca gctttttctc tgtattctaag ctgacagtgg | 600 |
| ataagtcccg gtggcagcag ggaaatgtgt ttagctgtag tgtcatgcat gaggccctgc | 660 |
| acaatcacta tacccagaaa tctctgagtc tgagcccagg caagaaggac cccaagttct | 720 |
| gggtcctggt ggtggtggga ggcgtgctgg cctgttactc tctcctggtg accgtggcct | 780 |
| tcatcatctt tgggtgcgc tccgggtga agttttctcg ctctgccgat gccccagcct | 840 |
| atcagcaggg ccagaatcag ctgtacaatg aactgaacct gggcaggcgg gaggagtacg | 900 |
| acgtgctgga taagcggaga ggcagagacc ccgagatggg cggcaaacca cggcgcaaaa | 960 |
| atccccagga gggactctat aacgagctgc agaaggacaa aatggccgag gcctattccg | 1020 |

-continued

```
agatcggcat gaagggagag agaagacgcg gaaagggcca cgacggcctg tatcagggat    1080
tgtccaccgc tacaaaagat acatatgatg ccctgcacat gcaggccctg ccacccaga     1139
```